(12) United States Patent
Rozenfeld et al.

(10) Patent No.: US 8,792,691 B1
(45) Date of Patent: Jul. 29, 2014

(54) SYSTEM AND METHOD FOR DETECTING MOTION PATTERNS OF IN VIVO IMAGING DEVICES

(75) Inventors: Stas Rozenfeld, Haifa (IL); Hagai Krupnik, Nofit (IL)

(73) Assignee: Given Imaging Ltd., Yoqneam (IL)

( * ) Notice: Subject to any disclaimer, the term of this patent is extended or adjusted under 35 U.S.C. 154(b) by 275 days.

(21) Appl. No.: 13/344,756

(22) Filed: Jan. 6, 2012

Related U.S. Application Data

(60) Provisional application No. 61/430,276, filed on Jan. 6, 2011.

(51) Int. Cl.
*G06K 9/00* (2006.01)
(52) U.S. Cl.
USPC .......................................................... 382/128
(58) Field of Classification Search
CPC ........... G06T 2207/10016; G06T 2207/10068; G06T 2207/30028; G06T 7/2053; H04N 5/232; H04N 5/77; H04N 5/772; H04N 5/783; H04N 7/18; A61B 1/00002; A61B 1/00009; A61B 1/00036; A61B 1/00045; A61B 1/041; A61B 2560/0209; A61B 5/0031; A61B 5/076; A61B 8/0841

USPC .......................................................... 382/128
See application file for complete search history.

(56) References Cited

U.S. PATENT DOCUMENTS

| | | | |
|---|---|---|---|
| 5,604,531 A | 2/1997 | Iddan et al. | |
| 7,009,634 B2 | 3/2006 | Iddan et al. | |
| 7,792,344 B2 * | 9/2010 | Wang et al. | 382/128 |
| 7,940,973 B2 * | 5/2011 | Lee et al. | 382/128 |
| 8,368,770 B2 * | 2/2013 | Glukhovsky et al. | 348/220.1 |
| 2009/0252390 A1 * | 10/2009 | Matsuzaki et al. | 382/128 |

\* cited by examiner

*Primary Examiner* — Tom Y Lu
(74) *Attorney, Agent, or Firm* — Pearl Cohen Zedek Latzer Baratz LLP

(57) ABSTRACT

A system and method for editing an image stream captured by an in-vivo imaging device that passes through the GI tract. The image stream including a plurality of image frames. A plurality of image sequences in the image stream may be detected. The plurality of image sequences may capture the same GI tract region. Some of the plurality of image sequences may be excluded from an edited image stream. The edited image stream may be displayed on a monitor.

24 Claims, 13 Drawing Sheets

Non-Progressive Movement

Bouncing-Progress Movement

SYSTEM AND METHOD FOR DETECTING MOTION PATTERNS OF IN VIVO IMAGING DEVICES

PRIOR APPLICATION DATA

The present application claims benefit from prior U.S. provisional application Ser. No. 61/430,276, filed on Jan. 6, 2011, entitled "SYSTEM AND METHOD FOR EDITING IN-VIVO IMAGE STREAMS CAPTURED IN OSCILLATING MOTION", incorporated by reference herein in its entirety.

FIELD OF THE INVENTION

Embodiments of the present invention relate to systems and methods for editing or presenting an image stream captured in-vivo. More specifically, embodiments of the present invention relate to systems and methods for editing a sequence of image frames captured by an in-vivo device traveling in a reverse direction or during oscillating motion.

BACKGROUND

Peristalsis within a gastro-intestinal (GI) tract may transport swallowed food and may aid in digestion and eventual evacuation. Peristalsis may result in pressure waves or contractions moving along the GI tract, which may result in the motility of a bolus or other object within the GI tract. The bolus may include an in-vivo imaging device able to acquire and transmit images of, for example, the GI tract while the in-vivo imaging device passes through the GI tract.

Rather than exerting a constant force, peristaltic contractions typically exert an oscillating force on the imaging device. The oscillating force pushes the in-vivo imaging device predominantly forward or in a positive direction (resulting in evacuation); however, local back-currents may pull the device backwards as it passes through the GI lumen. Positive/forward/progressive in the context of a device in the GI tract may mean in a direction along the GI tract from the mouth toward the anus.

Images captured while the imaging device is traveling in oscillating motion may be disorienting for a viewer, and may mostly include redundant image information, which may cause un-necessary long image streams. These images may also cause errors in automated tracking or processing systems. For example, when calculating a path-length traversed by the device, current systems may detect movement by changes between consecutive image frames. Such systems may be unable to distinguish between forward and backward movement of the imaging device. Such systems may add to the total path-length calculations, not only images captured during forward movement, but also images captured during backward movement or repeated forward movement through the same GI section due to back-tracking, thereby incorrectly determining that the imaging device has moved farther than it actually has.

There is a need for a system to accurately distinguish and edit image streams captured during oscillating movement of an in vivo device.

SUMMARY OF THE INVENTION

In an embodiment of the invention, a system and method is provided for editing an image stream captured by an in-vivo imaging device, for example, in one passage through the GI tract (from the mouth to the anus). The image stream may include a number of image frames. A first frame of the number of image frames, which is captured at a later time than a second frame of the number of image frames, may be determined to include an image of a region of the GI tract at an earlier relative position than the region in an image included in the second frame. The first or second frame may be excluded from an edited moving image stream. The edited moving image stream may be displayed. The segments of the image stream or frame sequences which are deleted may include portions captured when the device oscillates or travels back and forth in the same region of the body lumen (e.g. returning to the same position in the body lumen, or traveling in a complete loop).

In an embodiment of the invention, the image stream editing method may include identifying redundancy of images, estimating the direction and path-length traveled by the in-vivo imaging device, verifying the results, and excluding some image frames, while ensuring full area coverage of the imaged tissue and preserving natural flow of the sequence of moving image stream of the remaining (un-excluded) image frames.

In one embodiment, a method and system may receive a moving image stream and, based on the images in the image stream, may detect sequences within the image stream where the device does not progress along the GI tract. An edited image stream may be created including images not within the detected sequences.

BRIEF DESCRIPTION OF THE DRAWINGS

The principles and operation of the system and method according to the present invention may be better understood with reference to the drawings, and the following description, it being understood that these drawings are given for illustrative purposes only and are not meant to be limiting, wherein.

Figure 1:
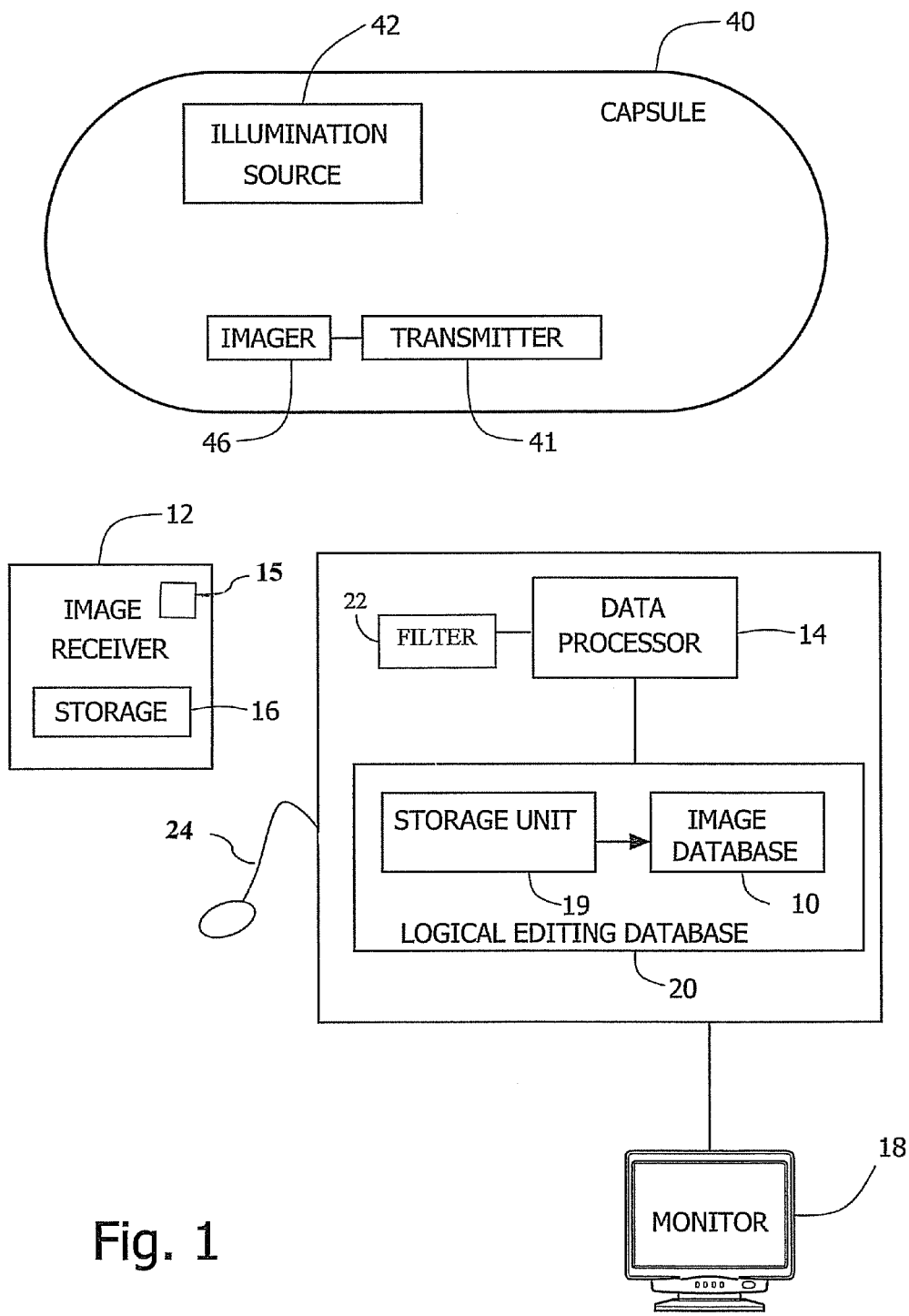
FIG. 1 is a schematic illustration of an in-vivo imaging system, according to an embodiment of the present invention.

It will be appreciated that for simplicity and clarity of illustration, elements shown in the figures have not necessarily been drawn to scale. For example, the dimensions and/or aspect ratio of some of the elements may be exaggerated relative to other elements for clarity. Further, where considered appropriate, reference numerals may be repeated among the figures to indicate corresponding or analogous elements throughout the serial views.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulates and/or transforms data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. Such apparatuses may be specially constructed for the desired purposes, or may include computers or processors selectively activated or reconfigured by a computer program stored in the computers. Such computer programs may be stored in a computer readable storage medium, such as, but is not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus. It will be appreciated that a variety of programming languages may be used to implement the teachings of the invention as described herein.

Embodiments of the invention may include an article such as a computer or processor readable medium, or a non-transitory computer or processor storage medium, such as for example a memory, a disk drive, or a USB flash memory, encoding, including or storing instructions, e.g., computer-executable instructions, which when executed by a processor or controller, carry out methods disclosed herein.

Some embodiments of the present invention are directed to a typically swallowable in-vivo device, such as an autonomous swallowable imaging device. Other embodiments need not be swallowable or autonomous, and may have other shapes or configurations. Devices according to embodiments of the present invention, including imaging, receiving, processing, storage and/or display units suitable for use with embodiments of the present invention, may be similar to embodiments described in U.S. Pat. No. 7,009,634 and/or in U.S. Pat. No. 5,604,531, each of which are assigned to the common assignee of the present invention and each of which are hereby incorporated by reference in their entirety. Of course, devices and systems as described herein may have other configurations and other sets of components.

Embodiments of the invention may edit a moving image stream including a series of images. Oscillating frame sequences (e.g. non-progressive motion sequences or bouncing-progressive motion sequences) that may include static or still sequences may be deleted which were captured when the device was traveling in a reverse direction, when standing still (static frames), and/or when the device was traveling in a forward direction but through an already captured region (eliminating images of "complete loops", e.g., redundant information captured while the device moves forward though the same region after back-tracking). In one embodiment, oscillating movement or motion of an in-vivo device may include movement or motion where some of the movement is not forward along the GI tract (from the mouth to the anus). Oscillating motion segments may include images of regions of the GI tract which have been imaged multiple or a plurality of times by the imaging device. Oscillating movement or motion may include movement where the device does not move forwards (towards the anus) or backwards (towards the mouth) but instead remains substantially still. An oscillating frame sequence shows images captured by a device when the device has non-progressive or bouncing-progressive movement, which may include static or still sequences. Each sequential frame in the remaining non-deleted portion of the edited moving image stream may have been captured in a forward motion along the GI tract, for example, so that no still and/or backwards motion is depicted. The exclusively forward moving (unidirectional, monotonic or direction preserving) image sequence may more accurately represent the GI tract and may be easier and more intuitive for a viewer to watch. In addition, redundant information captured while the device travels in the same region of the GI tract may be eliminated, hidden, merged or removed in order to make the edited image stream or movie shorter and, for example, quicker to review by a health care professional.

In some embodiments, the image sequence may be edited to maintain a natural flow of the sequence or movie, e.g., such that the viewer does not detect sudden changes in scenery, or sudden changes in the velocity or speed of the imaging device as a result of the editing or frame removal. In some embodiments, eliminating oscillating image sequences may cause abrupt changes, "jumps," or "skips" in the image sequence. Accordingly, when a significant number of consecutive frames are deleted or edited out (e.g., to eliminate a "complete loop"), embodiments of the invention may smooth the transition or jump between images between which frames have been deleted.

In some embodiments, a distance or path-length traveled by the imaging device between capturing sequential frames may be calculated or estimated, for example, based on the images, sensed position data (e.g. sensed by a position sensor), or a combination thereof. Distances, such as a total path length traversed or distances between frames, may be calculated by adding distances between consecutive frames of images captured when the device is exclusively moving forward through a progressive region (e.g., not through a region already traversed). In some embodiments, the distance may be a sum of positive values (e.g., when the device is moving forward) negative values (e.g., when the device is moving in a reverse direction) and/or zero values (e.g., when the device is still or static). Embodiments of the invention may ignore or subtract distances associated with images captured when the device is traveling in oscillating (e.g., non-progressive or bouncing-progressive motion that may include static image sequences or backwards movement or motion).

Since the GI tract has a curvilinear or winding path rather than a straight path, when described herein, "progressive" or "forward" motion and "reverse" may likewise be winding, for example, continuously changing in space to follow the curvature of the GI tract. Distances and movement when discussed herein are generally one-dimensional approximations of this movement. In one embodiment, progressive, forward, unidirectional or advanced movement along the length of the GI tract may advance along a curvilinear line laterally traversing the GI tract from a point of ingestion to a point of evacuation from the body. For example, the position within the GI tract may be measured along an imaginary line that runs along the longitudinal center axis of the GI tract. Forward and reverse (backward) motion may indicate an increase and decrease, respectively, in the path-length traveled along the axis, for example, from a point of ingestion to a point of expulsion. When discussed herein, the path-length traveled along the axis may measure the distance of the imaging device from a first point to a second point along the axis. However, the actual cumulative distance traveled from one point to another, for example, when considering back-and-forth movements along the length of the GI tract, may be longer than the measured path-length.

In one embodiment, an image stream captured by an in-vivo imaging device may be edited to produce an edited image stream. It may be determined that a first frame, which is captured at a later time than a second frame, images or includes an image of a region of the GI tract at an earlier relative position than the region imaged by the second frame. One of the image frames, the first or second frame, may be excluded or deleted from the edited image stream. When used herein an image being excluded or deleted from an edited moving image stream may mean that the image is never added to the edited moving image stream. In an embodiment where the edited moving image stream is created by marking or indexing frames from the original image stream, excluding or deleting image frames may include indexing or marking frames so that the frames do not appear in the resulting edited stream. Typically, a frame is captured at an earlier relative position than another frame if it is captured closer, in a linear sense, to the entry point of the GI tract (e.g., the mouth). Typically, forward motion is motion from the mouth towards the anus, when considered from a linear perspective (along the line of the GI tract). A frame captured at a later physical position has been captured when the capsule is further along in its progressive movement or motion.

Reference is made to FIG. 1, which schematically illustrates an in-vivo imaging system according to an embodiment of the invention.

According to some embodiments, the system may include an imaging device 40 for autonomously traveling and capturing images in-vivo. Device 40 may be a swallowable in-vivo capsule, but other sorts of devices or suitable implementations may be used. According to one embodiment, device 40 may communicate with an external receiving and display system to provide display of data, control, or other functions. Power may be provided by an internal battery or a wireless receiving system. Other embodiments may have other configurations and capabilities.

Device 40 may include an imager 46, for capturing images, an illumination source 42, for illuminating the body lumen, and a transmitter 41, for transmitting image and possibly other information to a receiving device. Transmitter 41 may include receiver capability, for example, to receive control information. An optical system, including, for example, lenses or mirrors, may aid in focusing reflected light onto the imager 46.

Preferably, located outside the patient's body in one or more locations, are an image receiver 12, preferably including an antenna or antenna array, an image receiver storage unit 16, and a data processor 15, a data processor 14, a data processor storage unit 19, and an image monitor 18, for displaying, for example, the images recorded by device 40. Preferably, the image receiver 12 and image receiver storage unit 16 are small and portable, and are worn on the patient's body during recording of the images.

According to embodiments of the present invention, data processor storage unit 19 may include an image database 10 and a logical editing database 20. In some embodiments, logical editing database 20 may be integrated into storage unit 19 or need not be used. According to one embodiment, logical editing database 20 may include criteria for editing a moving image stream, for example, including rules and logic for selecting images stored in the image database 10 that are captured when device 40 travels in progressive (monotonically forward) motion and not in any other motion pattern (non-progressive, still, bouncing-progressive or reverse) motion or, equivalently, rules for deleting images captured when device 40 does not travel in progressive (monotonically forward) motion. An edited sequence of the selected or non-deleted unidirectional (progressive motion) images may be displayed to the viewer as an edited moving image stream, e.g., in image monitor 18.

Storage units 19 and 10 may store data such as image frames, image streams, and edited image streams, and intermediate data or metadata such as transformation graphs or indexes.

According to one embodiment of the invention, data processor 14, data processor storage unit 19 and monitor 18 are part of a personal computer or workstation which includes standard components such as a processor, a memory, a disk drive, and input-output devices, although alternate configurations are possible, and the system and method of the present invention may be implemented on various suitable computing systems. An input device 24 may receive input from a user (e.g., via a pointing device, click-wheel or mouse, keys, touch screen, recorder/microphone, other input components) and send corresponding commands to trigger control of the computer components, e.g., data processor 14.

Data processor 14 or 15 may include any standard data processor, such as a microprocessor, multiprocessor, accelerator board, or any other serial or parallel high performance data processor. Image monitor 18 may be a computer screen, a conventional video display, or any other device capable of providing image or other data.

Imager 46 may be a complementary metal-oxide-semiconductor (CMOS) camera, such as a "camera on a chip" type CMOS imager specified by Given Imaging Ltd. of Israel and designed by Photobit Corporation of California, USA. In alternate embodiments, the imager 46 may be another device, for example, a charge-coupled device (CCD). The illumination source 42 may be, for example, one or more light emitting diodes, or another suitable light source.

In operation, imager 46 may capture images and send data representing the images to transmitter 41, which transmits images to image receiver 12 using, for example, electromagnetic radio waves. Image receiver 12 may transfer the image data to image receiver storage unit 16. After a certain period of time of data collection, the image data stored in storage unit 16 may be sent to the data processor 14 or 15 or the data processor storage unit 19 or 16, respectively. For example, the image receiver storage unit 16 may be taken off the patient's body and connected to the personal computer or workstation which includes the data processor 14 and data processor storage unit 19 via a standard data link, e.g., a serial or parallel interface of known construction. The image data may then be transferred from the image receiver storage unit 16 to the image database 10 within data processor storage unit 19.

Data processor storage unit 19 may store a series of images recorded by device 40. The images the device 40 records as it moves through a patient's GI tract may be combined consecutively to form a moving image stream.

Data processor 14 may analyze and edit the moving image stream, for example, according to the logical editing database 20, and provide the analyzed and edited data to the image monitor 18, where for example a health professional views the image data. Data processor 14 may operate or execute software which, in conjunction with basic operating software such as an operating system and device drivers, controls the operation of data processor 14. According to one embodiment, the software controlling data processor 14 may include code written, for example, in the C++ language and possibly alternative or additional languages, and may be implemented in a variety of known methods. Alternatively, data processor 15 may analyze and edit the moving image stream.

The image data collected and stored may be stored indefinitely, transferred to other locations, or manipulated or analyzed. A health professional may use the images to diagnose pathological conditions of for example the GI tract, and, in addition, the system may provide information about the location of these pathologies. While using a system where the data processor storage unit 19 or 16 first collects data and then transfers data to the data processor 14 or 15, respectively, the image data may not be viewed in real time, however, other configurations allow for real time viewing.

According to one embodiment, the device 40 may collect a series of still images as it traverses the GI tract, for example, oscillating with both progressive and non-progressive motion. The images may be later presented as, for example, a stream of images or a moving image of the traverse of the GI tract. The in-vivo imager system may collect a large volume of data, as the device 40 may take several hours to traverse the GI tract. The imager 46 may record images at a rate of, for example, four to forty images per second (other rates, such as two frames per second, may be used). The imager 46 may have a fixed or variable frame capture and/or transmission rate. When the imager 46 has a variable or adaptive frame rate (AFR), the imager 46 may switch back and forth between frame rates, for example, based on parameters, such as the device 40 speed or velocity, forward or reverse direction, estimated location, similarity between consecutive images, or other criteria.

Preferably, the image data recorded and transmitted by the device 40 is digital color image data, although in alternate embodiments other image formats may be used. In one example, each frame of image data includes 256 rows of 256 pixels each, each pixel including bytes for color and brightness, according to known methods. For example, in each pixel, color may be represented by a mosaic of four sub-pixels, each sub-pixel corresponding to primaries such as red, green, or blue (where one primary is represented twice). The brightness of the overall pixel may be recorded by a one byte (i.e., 0-255) brightness value. According to one embodiment, images may be stored sequentially in data processor storage unit 19. The stored data may include one or more pixel properties, including color and brightness.

A total of thousands of images, for example, over 300,000 images, may be recorded during the complete passage of the device 40 through the body and combined into a moving image stream. Many of these frames may be repeated (imaging the same region), for example, when the imaging device is stuck (in a static state) or traveling backwards (in non-progressive motion). Embodiments of the invention may identify such duplicate passes and take action on the duplicate passes.

According to an embodiment of the invention, the data processor 14 may include an editing filter 22 for editing the moving image stream. Editing filter 22 may delete images captured by the device 40 traveling in non-progressive motion and progressive motion (when device 40 moves progressively after moving non-progressively, creating a duplicate pass). Deleting or excluding non-progressive frames may significantly reduce the number of images in the moving image stream. When used herein, deleting or excluding images may include, when creating an edited stream, not including the images in the edited stream. Deleting or excluding may include removing images from an image stream.

Editing filter 22 may be an editing filter processor or may be implemented by data processor 14 or 15. While the editing filter 22 is shown in FIG. 1 as being separate from and connected to processor 14, in some embodiments editing filter 22 may be a set of code or instructions executed by processor 14 or 15 (e.g., may be processor 14 or 15). Editing filter 22 may be or include one or more dedicated processors. Editing filter 22 may generate an edited moving image stream including a proper (non-trivial) subset of an initial or input set of images (the remaining subset may be removed, deleted, skipped, jumped or hidden from view). The editing filter 22 may use image analysis capabilities from logical database 20 to detect the type of motion of the device (e.g., progressive or non-progressive) when capturing the images. The editing filter 22 may select only a subset of images captured when device 40 travels with progressive motion and/or delete images captured when device 40 travels with non-progressive motion to form a unidirectional progressive edited image stream.

The image recordation rate, the frame capture rate, the total number of images captured, the percentage of frame reduction due to deleting non-progressive images, the total number of images in the edited moving image, and the view time of the edited moving image, may differ between image sequences and may each be fixed or variable.

While, preferably, information gathering, storage, and processing are performed by certain units, the system and method of the present invention may be practiced with alternate configurations. For example, the components gathering image information need not be contained in a capsule, but may be contained in any other vehicle suitable for traversing a lumen in a human body, such as an endoscope, stent, catheter, needle, etc.

An imager in or affixed to the device 40 may capture images from both the forward and reverse directions consistent with the device's direction of travel. These images may be displayed, in sequence, to generate a moving image stream of the GI tract. In sequence, non-progressive motion may cause a first frame, which is captured at a later time than a second frame, to image a region of the GI tract at an earlier relative position than the region imaged by the second frame. In some embodiments, oscillating motion may cause two frames, not necessarily consecutive, to capture the same GI tract region. In some cases, the channel of the GI tract may appear similar in both the forward and reverse direction and a viewer may be uncertain of the relative position of the frames and the direction in which the device 40 is traveling.

In some embodiments, a capsule may have more than one imaging system (each comprising an imager and an optical system), for example two imaging heads. In one example, one imaging head may capture images in a forward looking direction, and another may capture images in a backward looking direction. Images from each head may be analyzed, for example as separate image streams. Determination of motion direction and or speed of the capsule may be performed based on one stream (e.g. images captured by a first imaging system) or using data captured by the plurality of imaging systems. An editing filter or processor (e.g., editing filter 22 and/or processor 14 or 15 of FIG. 1) operating according to embodiments of the invention may automatically identify and delete sequential images which include images of, represent, or capture oscillating motion through the body lumen. In one embodiment, the editing filter may delete any image frame that includes an image of, images, or captures a region of the body lumen at a position less or earlier than or equal to a position of a most advanced previously captured frame(s) (in a positive direction of the body lumen). In one embodiment, the filter may delete a first or second image frame, where the first frame, which is captured at a later time than a second frame, images a region of the GI tract at an earlier relative position than the region imaged by the second frame. These deleted images may have been captured while the device 40 was traveling in reverse motion, with no motion, or backtracking in a forward direction through an already traversed region. Removing these frames may not only simplify the orientation of the device 40 motion (only the forward direction frames are used), but also reduce the number of frames in the moving image stream to reduce viewing time.

Peristaltic forces may cause longitudinal and/or oscillating waves to propagate an autonomous in-vivo imaging device 40 through the body lumen. These waves may propagate the device 40, on average, in a forward direction (from the mouth to the anus) through the body lumen, but may include local fluctuations or back-currents, that pull the device 40 backward. Accordingly, the device 40 may move in a forward-backward oscillating motion, and/or may substantially not move for periods of time during which images are captured. Oscillating motion may include reverse or backward motion, no motion (static states) as well as forward motion through a region the device 40 has already traveled through due to back-tracking. Forward and backward may be directions measured relative to a center longitudinal axis of the GI tract and may indicate an increase or decrease, respectively, in the path-length traveled in a predominant direction along the axis. The path-length may be an absolute or relative distance along the center longitudinal axis of the body lumen, for example, measured from an initial point for the entire body lumen (e.g., the mouth or the beginning or end of the esophagus) or an initial frame for each of a number of segments or portions of the image stream.

Figure 2A:
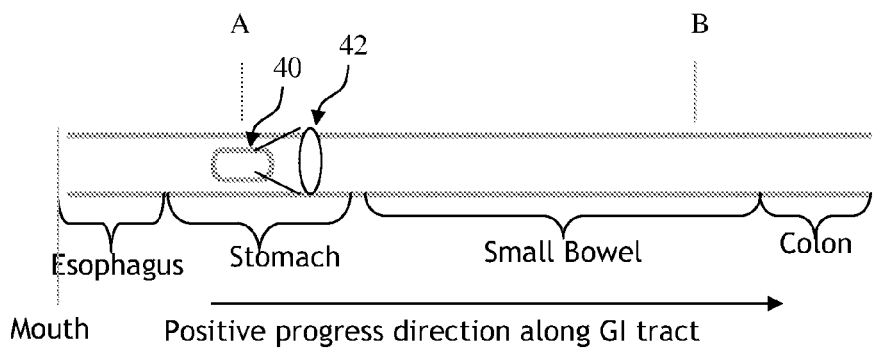
FIGS. 2A and 2B are schematic illustrations of a device traveling in an oscillating manner, according to embodiments of the present invention.
Figure 2B:
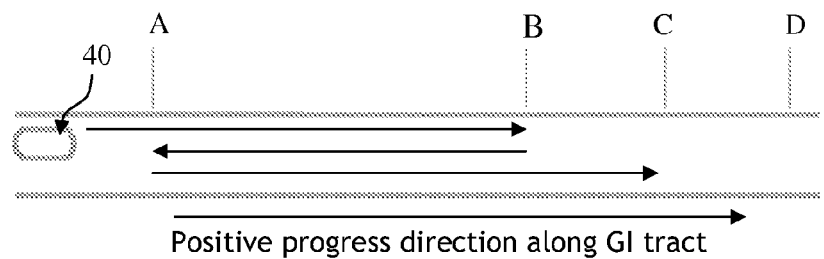

Reference is made to FIGS. 2A and 2B, which schematically illustrate a device traveling in an oscillating manner (e.g. non-progressive or bouncing-progressive), according to embodiments of the invention. Oscillating movement sequences may depict complex motion patterns of the device. The complex motion patterns may include a plurality of different types of simple or uniform motion patterns. Uniform motion patterns may include a single type of movement. For example the following types of movement may be addressed as uniform motion:
1. movement in a monotonic forward direction (e.g. monotonically forward or progressive) along the GI tract;
2. movement in a monotonic backward (monotonically backward) direction along the GI tract; and
3. still, static or stagnant periods, in which the imaging device remains substantially in the same position in the GI tract.

According to some embodiments, a combination or proportion of different types of uniform motion patterns in the oscillating motion pattern may differentiate between a non-progressive motion pattern and a bouncing-progressive motion pattern. The non-progressive motion pattern may include a similar proportion of forward and backward repetitive movements of the imaging device. The bouncing-progressive motion pattern may include, for example, more forward movements than backward movements of the imaging device along the GI tract.

In FIG. 2A, at a given time, $t_0$, the imaging device may be at "A" while position "B" may be the most advanced previously recorded position (at time $t_{-1}$, i.e. before $t_0$) occupied by the device 40. In some cases, the device 40 may move back and forth between points A and B in the GI tract. For example, the device 40 may capture image segments during the back and forth movement or motion, which may capture the same in-vivo regions several times during the imaging procedure. For example, the image stream may include 10-20 repetitions of image segments capturing structures between A and B. Such a motion pattern is addressed in this invention as "oscillating movement".

The editing filter may discard all frames captured between positions A to B (except for frames captured in one pass) until the device 40 passes position B, and resumes its forward motion towards evacuation from the GI tract (e.g., to an in-vivo region which has not yet been imaged). The device may travel along the GI tract, typically starting from the mouth and traversing the GI tract through the esophagus, stomach, small bowel and colon. Such movement may be defined to be a "positive" direction of movement of the capsule through the GI tract. Generally the "time" associated with a frame is the capture time of the frame, relative to a start time of image stream capture (time elapsed, for example, from the beginning of the procedure or from a predetermined point or time) or the actual time of capture. Other times may be associated with an image frame. If the device 40 at time, $t_0$, is located at a current position "A" less than or equal to the most advanced position "B" (e.g., closer in a linear sense to the entry point), the device 40 may have a stagnant or reverse movement. Since the device 40 was at position B at time $t_{-1}$, it may have already passed position A at a previous time, $t<t_{-1}<t_0$. Therefore, an imaged region 42 captured by the device 40 at position A at time $t_0$ may have already been captured by the device 40 at the previous time t. Accordingly, the frame capturing imaged region 42 when the device 40 is at position A, at time $t_0$, may be discarded, for example, to avoid repetition of capturing the same region in the edited image stream.

An example of bouncing-progressive motion pattern of the imaging device 40 is illustrated in FIG. 2B. FIG. 2B shows four incrementally progressive positions along the GI tract, "A," "B," "C," and "D." During bouncing-progressive motion, the device 40 may travel in a forward motion from an initial position A at time $t_0$ to position B at later time $t_1$, $t_1 > t_0$. At a later time $t_2 > t_1$, the device 40 may regress back to initial position A, then progress (e.g., move) to progressive position C at later time $t_3 > t_2$. The device 40 may continue such bouncing-progressive motion by regressing back to position B or to another position backward from position C and then progress or move to progressive position D. Such movement may cause the device 40 to capture images of regions previously captured, e.g., in regressive (backward) movement or motion of the device 40 or during forward movement of the device 40 (e.g., to a point in the GI tract which has already been reached and imaged at a previous time).

In some embodiments, if the position of the imaged region 42 of a current frame is more positive or advanced than that of the most advanced previously captured frame, then the frame may have been captured during progressive motion of the device 40 and may be selected for and included in the edited image stream. Conversely, if the position of the imaged region 42 of the current frame is more negative or less advanced than the most advanced previously captured frame, then the frame may have been captured during non-progressive, backward or bouncing-progressive motion of the device 40 and may be deleted (not selected for or excluded from) from the edited image stream.

In some embodiments, the image stream may be divided into sub-segments or portions of the moving image stream for evaluating motion separately for each segment. The image stream may be divided, in some embodiments, quantitatively, e.g., into a predetermined number of segments or into segments of an equal predetermined length, time span or number of frames, or in other embodiments, qualitatively, e.g., grouping images with similar image characteristics, anatomical structures, lighting, contrast, brightness, lumen size, etc. For qualitative division, embodiments of the invention may use a similarity filter to select segments imaging the same in-vivo region, e.g., the small bowel.

In some embodiments, a change $d(i,i+1)$ in the position of an imaging device during capturing of frames (i) and (i+1) may be estimated for any pair of consecutive frames of a captured image sequence.

Figure 3:
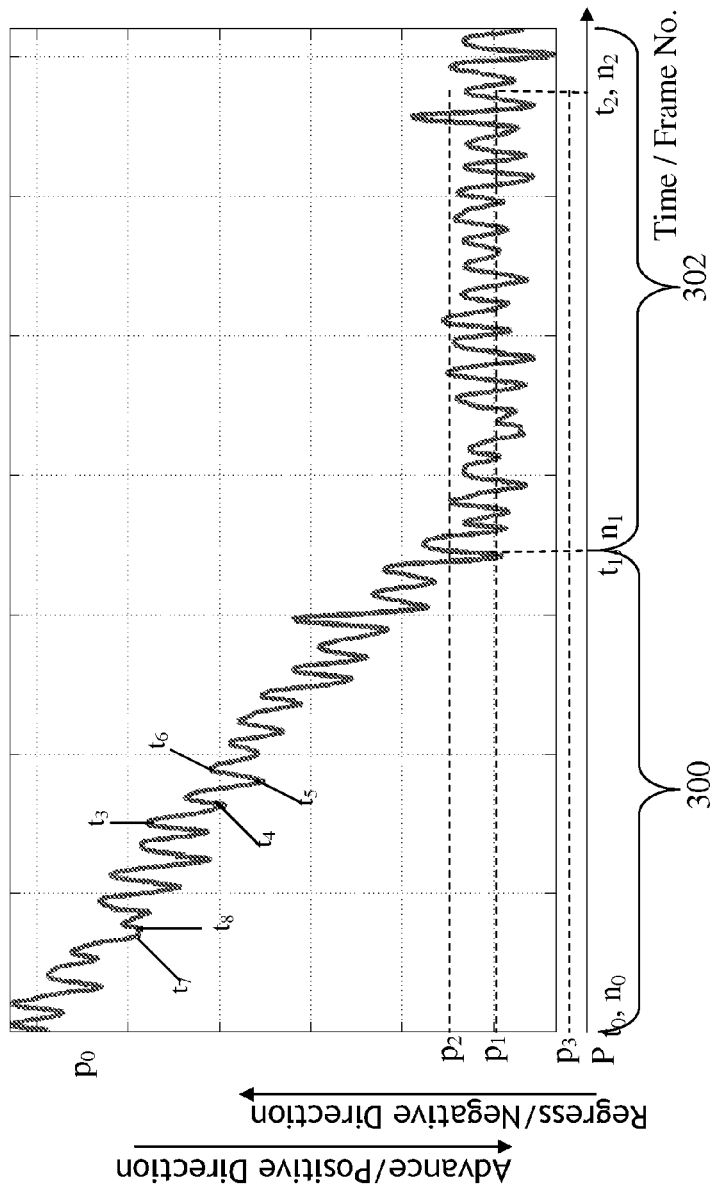
FIG. 3 illustrates a schematic graph of estimated position of the imaging device in the GI tract (y-axis) vs. frame number (x-axis) in an initial image sequence, according to an embodiment of the invention.

Reference is made to FIG. 3, which illustrates a schematic graph of estimated position of the imaging device in the GI tract (y-axis) vs. frame number (x-axis) in an initial image sequence, according to an embodiment of the invention.

In some embodiments, once a "reference frame" $i_0$ is selected (for example, the "reference frame" may be the first image frame of a sequence of image frames) the position $d(i_0, i)$ of frame i of the sequence of frames, relative to the position of the "reference frame", may be calculated according to the following equations; other equations may be used:

$$d(i_0,i) = d(i_0,i_0+1) + d(i_0+1,i_0+2) + \ldots + d(i-1,i), \text{ for } i > i_0$$

$$d(i_0,i) = -(d(i_0,i_0-1) + d(i_0-1,i_0-2) - \ldots - d(i+1,i)), \text{ for } i < i_0$$

FIG. 3 may be a representation of all relative positions per each image frame of the sequence of image frames.

In FIG. 3, the position of the regions imaged by sequential frames may oscillate over time moving forward and backwards along the length of the GI tract (e.g., indicated by a decreasing and increasing value, respectively, in the (y) axis of the graphs of FIG. 3). The oscillation of frames may correlate to oscillation of the in-vivo imaging device within the GI tract. A constant position among frames may indicate no motion (a static or stagnant state of the imaging device and/or the GI tract).

FIG. 3 shows the relative positions of regions of the GI tract imaged during a bouncing-progressive motion or movement segment 300 and a non-progressive movement segment 302 along the GI tract. The cumulative change in position of the frames represented in the bouncing-progressive movement segment 300 of FIG. 3 (between $t_0$ to $t_1$) is in a positive direction along the GI tract (e.g., the initial position $p_0$ at time $t_0$ is less advanced through the GI tract than the position $p_1$ at time $t_1$). However, locally, at smaller time or frame intervals (e.g., 2-40 seconds or 1-20 frames, respectively), the imaging device and thus, the captured frames may change motion directions, for example between progressive (forward, e.g. between $t_3$ and $t_4$) and non-progressive (backward, e.g. between $t_5$ and $t_6$, or static, e.g. between $t_7$ and $t_8$) motion. When used herein, "oscillating motion," may refer to cyclic, repetitive or periodic motion such as bouncing-progressive motion, non-progressive motion, and/or a combination thereof. Segment 302 represents an oscillating non-progressive motion pattern of the imaging device in a GI tract. As shown in FIG. 3, the estimated or calculated position of the imaging device from the reference point at time $t_1$ is position $p_1$ and similarly, the position at time $t_2$ is also position $p_1$. During the period between times $t_1$ and $t_2$, the device moves back and forth between positions $p_2$ and $p_3$.

An editing module may compare the position of the imaging device during the capture of consecutive frames (i) and (i+1) or non-consecutive frames (i) and (i+n), where n is an integer greater than 1. In one example, each frame (i) may be compared with a frame (i+n) that is the most-advanced frame previously captured in the same segment as frame (i).

To estimate the progress or movement $d(i,i+1)$ of the imaging device between capturing two consecutive frames (i) and (i+1) the editing module may initially measure the distortion (e.g., stretching and shrinking) between these frames. As the device moves towards an imaged area, the size of objects may grow larger (e.g., "stretching"), and when the device moves away from an object, the object's imaged size or its pixel area in the image may become smaller (e.g., "shrinking"). In one example, the editing filter may measure distortion as a change in the number of pixels (e.g., pixel area) imaging the same target image object in each frame. When the number of pixels imaging the structure increases in a subsequent frame, the imaged structure may have stretched and the device may be determined to have moved towards the object, while when the number of pixels imaging the structure decreases in a subsequent frame, the imaged structure may have shrunk and the device may be determined to have moved away from the imaged object.

Figure 4:
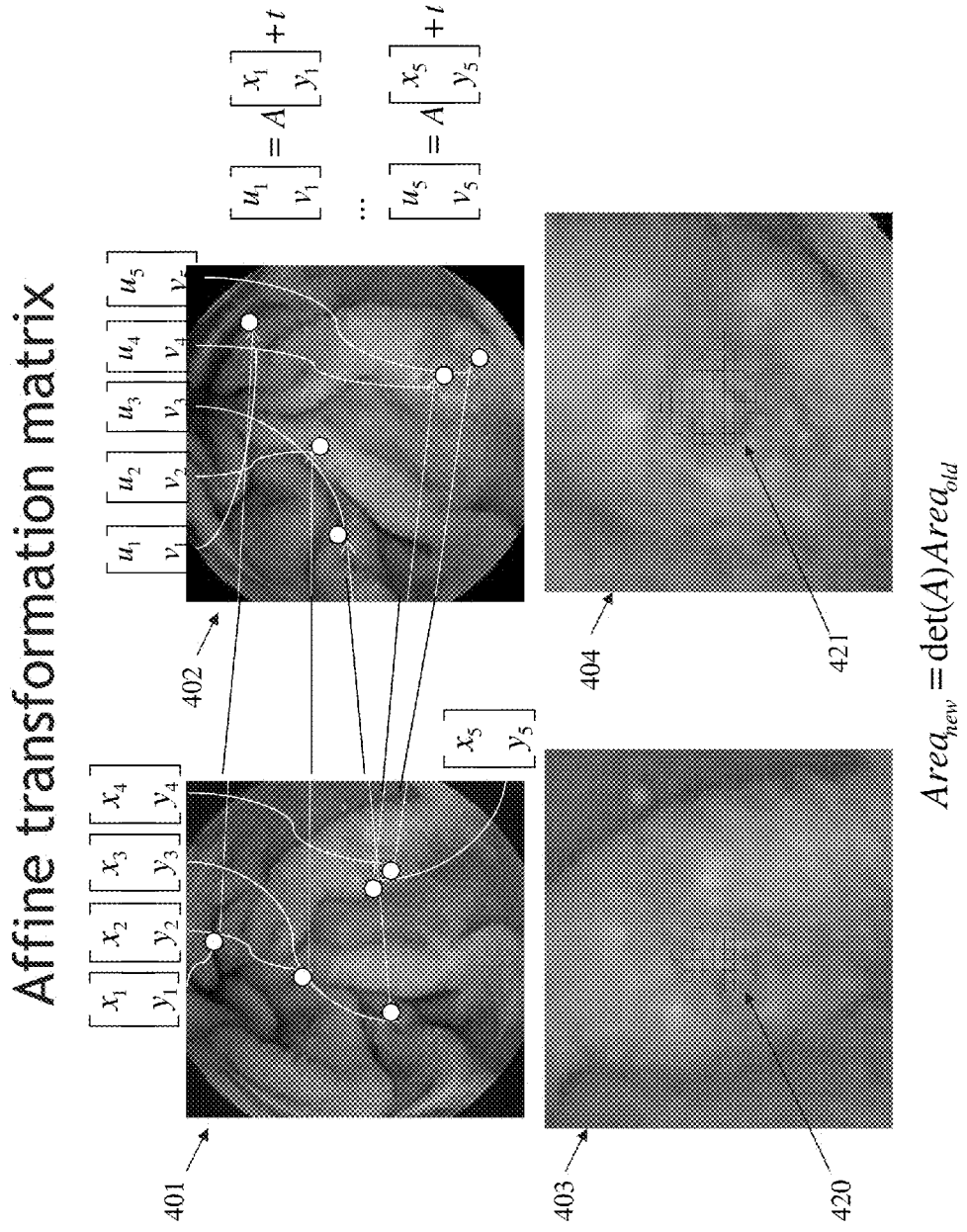
FIG. 4 is a schematic illustration of a motion estimation mechanism, according to an embodiment of the invention.

Reference is made to FIG. 4, which is a schematic illustration of a motion estimation mechanism, according to an embodiment of the invention. FIG. 4 includes sequential image frames i and i+1, or 401 and 402, respectively, imaging substantially the same region of the GI tract, captured at two different times, e.g. at sequential time periods. In one example, image frames 401 and 402 may have correlated points representing the same target structure or object positioned at respective image frame coordinates $(x_1,y_1)$ in frame 401 and $(u_1,v_1)$ in frame 402. Similarly, one or more additional points in frames 401 and 402 at coordinates $(x_2,y_2)$, $(x_3,y_3), \ldots, (x_j,y_j)$ in frame 401 and coordinates $(u_2,v_2)$, $(u_2,v_3), \ldots, (u_j,v_j)$ in frame 402 may be correlated, respectively. An area 420 of pixels in frame 403, (which is a zoomed or enlarged portion of frame 401) may image the same target structure as an area 421 of correlated pixels in frame 404 (which is a zoomed or enlarged portion of frame 402).

In some embodiments, for the most pairs of consecutive frames (i) and (i+1) there may exist an affine transformation matrix $\text{Aff}_{i,i+1}$. (other or different formulas or transformations may be used):

$$\text{Aff}_{i,i+1} = [A_{i,i+1} | T_{i,i+1}],$$

$$A_{i,i+1} = \begin{bmatrix} a_{i,i+1} & b_{i,i+1} \\ c_{i,i+1} & e_{i,i+1} \end{bmatrix} \quad T_{i,i+1} = \begin{bmatrix} t_{i,i+1} \\ \tau_{i,i+1} \end{bmatrix}$$

$A_{.,.}$ is referred to as "distortion matrix" and $T_{.,.}$ is referred to as "translation vector". The affine transformation matrix may be estimated by a processor and may provide the following constraint on a change in location between the consecutive image frames (e.g. frames 401, 402) of their correlated pairs of points (e.g., $(x_j, y_j)$ and $(u_j, v_j)$) (other or different formulas may be used).

$$\begin{bmatrix} u_j \\ v_j \end{bmatrix} = A_{i,i+1} \begin{bmatrix} x_j \\ y_j \end{bmatrix} + T_{i,i+1} \quad (1)$$

In the example provided in FIG. 4, j may be any of: 1, 2, 3, 4 or 5.

In some embodiments, for any target structure captured by two compared frames (with existing affine transformation matrix), the ratio between the two areas occupied by the target structure in the two frames, may be equal to the determinant of the distortion matrix (det(A)). For example:

$$\frac{\text{Area}_{new}}{\text{Area}_{old}} = \det(A_{i,i+1})$$

A determinant of less than 1 may indicate that the size of the target structure in frame i is smaller than the size of the target structure in its preceding compared frame, thereby indicating that the in-vivo imaging device is more distant from the target structure in frame i than it is in its preceding compared frame. A determinant of greater than 1 may indicate that the size of the target structure in frame i is larger than the size of the target structure in its preceding compared frame, thereby indicating that the in-vivo imaging device is closer to the target structure in frame i than it is in its preceding compared frame. A determinant equal 1 may indicate no substantial distortion of the target structure between the two consecutive frames; thereby it may indicate that the distance of the in-vivo imaging device from the target structure in both frames is substantially the same.

The factor of the area change between frames may be multiplicative, which is consistent with the multiplicative nature of determinants and the nature of affine transformation matrix. Accordingly, a factor of the cumulative area change of a sequence of frames between non-sequential frames (e.g. frame k to frame l+1) is equal to the product of the determinants of the distortion matrices of each pair of frames present in the sequence between the non-sequential frames, which by the multiplicative property is equal to the determinant of the products of the distortion matrices themselves. That is, the cumulative transformation or area change of pixels representing a target structure among a number of frames may be, for example (other or different formulas may be used):

$$\text{area ratio}_{k \to l+1} = \det(A_{k,l+1}) = \det(A_{k,k+1} A_{k+1,k+2} \ldots A_{l,l+1}) = \det(A_{k,k+1}) \det(A_{k+1,k+2}) \ldots \det(A_{l,l+1}) \quad (2)$$

Although factors of area change between frames may be multiplicative, the distance (e.g. between frames) is typically additive. Therefore, the processor may use a logarithmic function, for an estimation of motion of the in-vivo imaging device between sequential frames i and i+1, for example (other or different formulas may be used):

$$d(i,i+1) = \log(\det(A_{i,i+1})) \quad (3)$$

That is, the cumulative distance or motion of the sequence of a number of frames between non-sequential frame k and frame l+1 may be, for example (other or different formulas may be used):

$$d(k,l+1) = \log(\det(A_{k,l+1})) = \log(\det(A_{k,k+1} A_{k+1,k+2} \ldots A_{l,l+1})) = \log(\det(A_{k,k+1})) + \log(\det(A_{k+1,k+2})) + \ldots + \log(\det(A_{l,l+1})) = d(k,k+1) + d(k+1,k+2) + \ldots + d(l,l+1) \quad (4)$$

During forward motion of the capsule, the area of an object captured in an image may increase (e.g., as the object gets closer to the imaging device), and the value of det(A) may be larger than 1, that is the value of log(det(A)) may be larger than 0. During backward motion of the in-vivo imaging device (e.g. the capsule), the area of an object captured in an image may decrease (e.g. as the object gets farther away from the imaging device), and the value of det(A) may be less than 1, that is the value of log(det(A)) may be less than 0. When the capsule stays at substantially the same distance from the object (e.g. when the capsule is substantially still), the value of det(A) equals 1, that is the value of log(det(A)) equals 0.

Equation (4) may be used to estimate the distance (e.g., a scaled distance) between two frames k and l+1 (e.g., which may be non-consecutive). Accordingly, the processor may determine or estimate the distance between any two non-consecutive frames, for example, in any part of a moving image stream, without calculating the distances between intervening pairs of frames. Furthermore, equation (4) may indicate the direction of travel between frames and, for example, may be negative during reverse motion, positive during progressive motion, and zero during static motion.

In order to estimate $\text{Aff}_{i,i+1}$ (and thus estimate d(i,i+1)) for a pair of consecutive frames (i) and (i+1), the processor may attempt the following registration process according to one embodiment of the invention. According to one embodiment, the registration attempt between frame i and frame i+1 may include, for example (other steps may be used):

Harris corner detector is applied to frame (i) in order to identify "corner-like" points Normalized cross-correlation is applied in order to find correlated points or matching points in frame i+1, which correlate to the points identified in frame i Due to the un-supervised nature of correlation process there are outliers among the established pairs of correlated points. RANSAC procedure is applied in order to eliminate such outliers.

All of the remaining pairs of correlated points (which were not defined as outliers) are used to estimate the affine transformation matrix as defined in equation (1), via least square error approach.

As a pre-process of editing oscillating image streams, according to embodiments of the invention, the above registration attempt may be performed per each pair of consecutive frames (i.e. between frames i and i+1). The registration process may fail for a few reasons, for example, too few correlated pair of points are generated in step 2 above, RANSAC process is too diverse (e.g. it detects too many outliers) or $\det(A_{i,i+1})$ is suspiciously far from 1 (e.g. $\det(A_{i,i+1}) > 1.2^2$ or $\det(A_{i,i+1}) < 0.8^2$.

Figure 5:
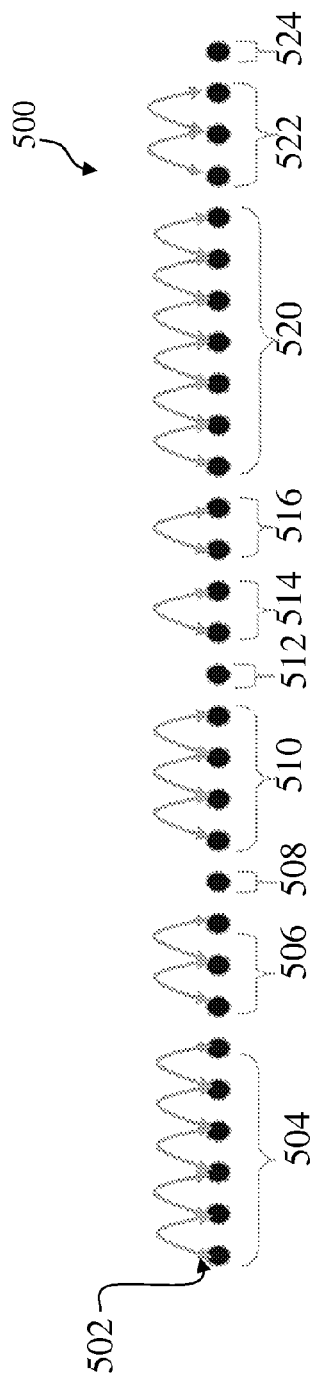
FIG. 5 is a schematic illustration of frames of an image stream sequence divided into a number of sub-sequences, according to an embodiment of the invention.

Reference is made to FIG. 5, which is a schematic illustration of frames of an image stream sequence divided into a number of sub-sequences, according to an embodiment of the invention. According to FIG. 5, the arrows illustrate a successful registration process between the two consecutive frames that the arrows connect. Sub-sequences 504-524 of FIG. 5 may be grouped when the registration is successful for each adjacent pair of frames within a sequence. Once the registration process is un-successful between two adjacent frames (e.g., no arrow connects between the two frames), a sub-sequence is finalized, while a new sub-sequence is built, as long as the registration process is successful between every following two consecutive frames i and i+1. Since the basic assumption in one embodiment is that the affine transformation matrix is only relevant between two consecutive frames, i.e., an estimate of the imaging device's progress or movement along the GI tract may be provided per each pair of consecutive frames, therefore the entire editing process of the entire image stream is performed for each sub-sequence alone.

Figure 6:
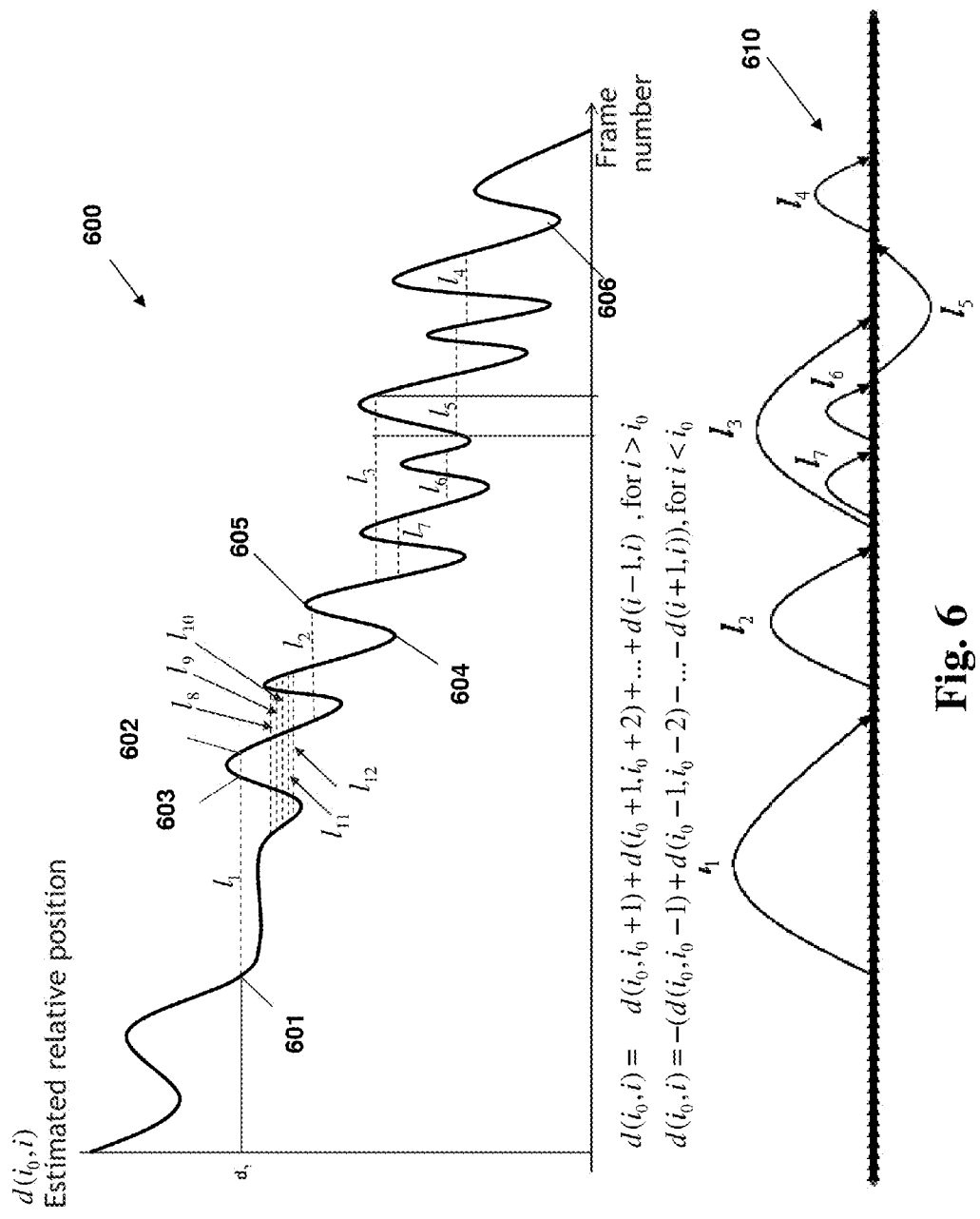
FIG. 6 illustrates a schematic graph of the estimated position of an imaging device capturing sequential frames, and a directed graph associated with the position graph, according to an embodiment of the invention.

Reference is made to FIG. 6, which illustrates a schematic graph of the estimated position of an imaging device capturing sequential frames, and a directed graph associated with the estimated position graph, according to an embodiment of the invention. An initial image sequence may be captured by the device (e.g., device 40 of FIG. 1) moving in a combination of forward, backwards and static motion or movement (which combination may be defined as oscillating motion pattern, as shown in FIG. 3). Sequential frames of the initial image sequence may include images of regions of the GI tract captured in both a relatively forward and reverse direction. Graph 600 shows the positions of sequential frames in the initial sequence, which oscillate back and forth relative to the chosen "reference frame" $i_0$ (captured during forward and backward movement of the imaging device). The peaks and troughs (e.g., local maxima and minima) of graph 600 may indicate still or no motion of the device (e.g., with a zero slope or deviation in the (y)-axis) as it changes directions, for example, from backward to forward and from forward to backward motion.

In the example shown in FIG. 6, a negative change in the position (y)-axis indicates a forward or positive motion in the region of the GI tract imaged by sequential frames and a positive change in the position (y)-axis indicates a backward or negative motion in the region of the GI tract imaged by sequential frames. In an alternative embodiment, a negative (y)-axis may indicate regressive motion and a positive (y)-axis may indicate progressive motion. A constant value in the position (y)-axis may indicate approximately no motion.

Frames associated with a monotonic (e.g., unidirectional, in this example, decreasing or non-increasing) position function may have unidirectional (e.g., progressive) motion. Conversely, frames associated with a non-monotonic (e.g., bi-directional) position function may be associated with bi-directional (e.g., oscillating) motion. Frames associated with non-monotonic segments of graph 600 may be excluded, edited, deleted, spliced, discarded, or not selected, to generate a monotonic graph, which includes only the selected images of the edited image sequence.

A jump candidate (or loop), according to some embodiments, may be defined as a number or sequence of consecutive image frames, where the first frame (the start frame of the jump candidate) and the last frame (the end frame of the jump candidate) are captured at approximately the same relative position in the GI tract. The portion of the GI tract depicted in the frames may portray the same region in the body lumen, and may be captured at the same relative position from the position of capturing reference frame $i_0$. A jump candidate may include a sequence of consecutive images which may be associated, or may correspond to, a detected oscillating motion segment of the imaging device along the GI tract. Detected oscillating motion segments may include images of regions of the GI tract, the image regions having been imaged repetitively, e.g. a plurality of times, by the imaging device.

Based on the position estimation graph 600, a mechanism for generating jump candidates may be created according to an embodiment of the invention. A number (e.g., a large number) of jump candidates (e.g., illustrated in FIG. 6 as dashed horizontal lines, $l_n$,) may be generated by a processor for potentially editing the initial image stream. Each dashed horizontal line $l_n$ may represent a jump candidate, or a back-and-forth loop motion or oscillation bridging the start frame and the end frame of the loop. For example, the frame at position 601 may be a start frame of loop $l_1$, and the frame at position 602 may be an end frame of the loop $l_1$. In one embodiment, the start frame and the end frame may image approximately the same position along the GI tract or distance from a reference position. For example, frames 601 and 602 may both image positions along the GI tract located at a distance $d_1$ from the position of a reference frame or point $i_0$.

According to some embodiments, once jump candidates or loops are created, they may undergo a validation step. A valid jump candidate may be, for example, a sequence such that if all frames between the start frame and the end frame of the jump sequence were to be deleted, no region of the GI tract imaged in the original image stream would lack coverage, coverage being the capture of images of the region. Such validation performed per each jump candidate, may include verification that if all frames within the start frame and the end frame of the jump were excluded from the edited image stream, no GI tract coverage of the tissue imaged in the original image stream is lost, and the edited image stream maintains smoothness and natural flow. Thereby, a set of valid jump candidates may be generated.

Once a number of valid loops or jump candidates are generated, the processor may select an optimal valid sub-set of one or more valid jump candidates to be excluded from the initial image sequence. For example, since $l_3$ and $l_5$ overlap (e.g., have frames imaged in overlapping regions or positions in the GI tract), the set $\{l_i, l_2, l_3, l_4, l_5\}$ is invalid. In another example, the set $\{l_i, l_2, l_4, l_5, l_6, l_7\}$ is valid, since there are no overlapping regions or positions in the GI tract between the imaged frames of the jump candidates included in the set $\{l_i, l_2, l_4, l_5, l_6, l_7\}$.

In some embodiments, the directed graph 610 associated with the position estimation graph 600 and valid jump candidates/loops may be built such that for each frame a node is defined. Then, for each pair of consecutive frames a directed edge is defined between the frames' corresponding nodes, e.g. a directed edge is defined between a node of one frame to a node of its successive frame. For each valid jump candidate, a directed edge is defined between the first node (corresponding to the first or start frame of the jump candidate) and the last node (corresponding to the last or end frame of the jump candidate). That is, a directed edge for a valid jump candidate is not necessarily defined between two adjacent frames, but rather between relatively distant frames.

To select the optimal (final) valid subset of valid jump candidates to be excluded from the image sequence, an editing mechanism using, for example, graph theory logic, may be used. The editing mechanism may be used in order to build directed graph 610 associated with the captured sequence of images and valid jump candidates. The editing mechanism may also find the shortest path between two nodes associated with the first and the last frames of the sequence in graph 610, e.g. using Dijkstra's algorithm, Bellman-Ford algorithm, A* search algorithm, Floyd-Warshall algorithm, or any other distance or path calculator or combination thereof.

Figure 7:
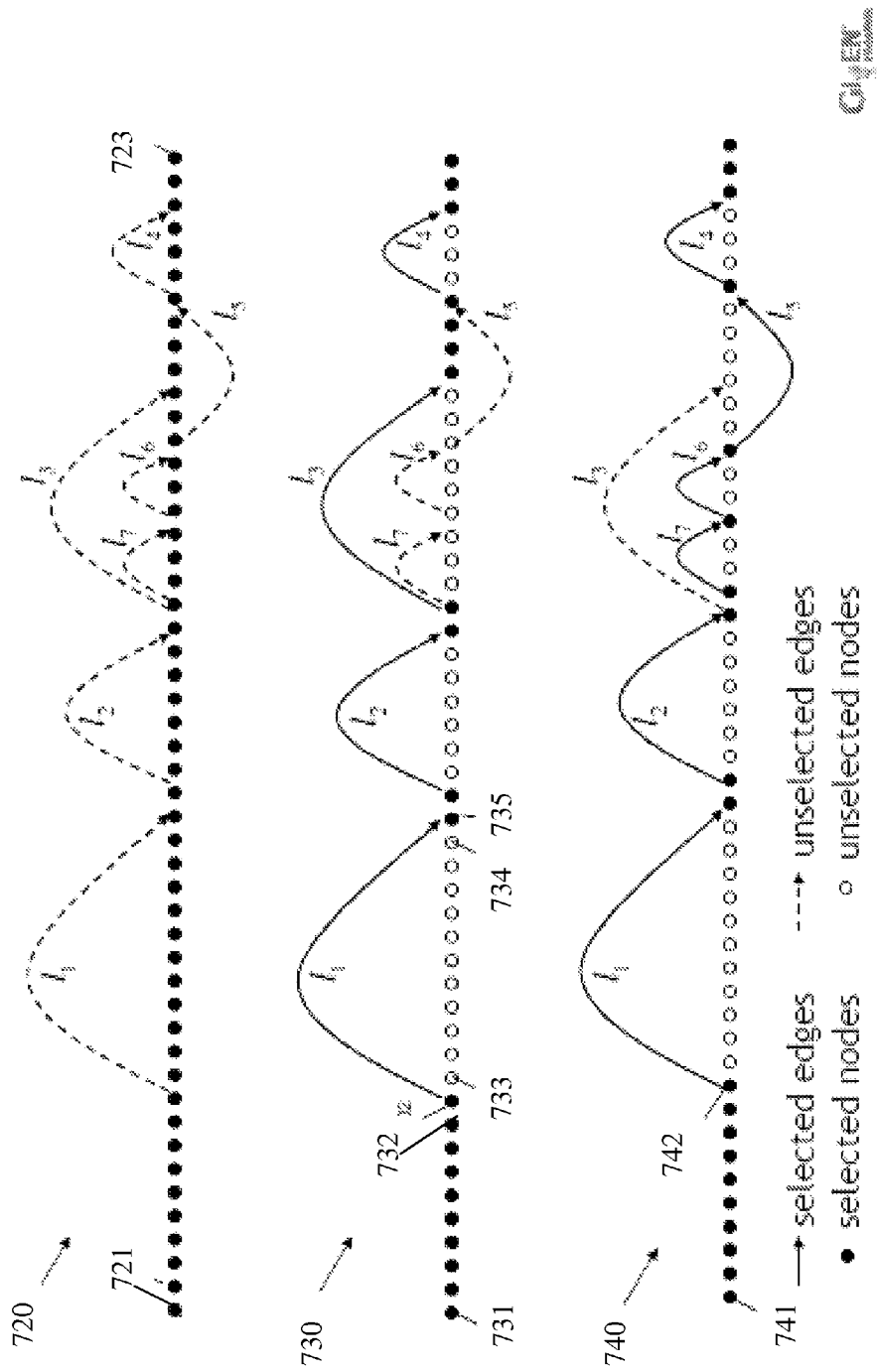
FIG. 7 includes a number of possible paths through the graph representing a number of possible edited image sequences, according to an embodiment of the invention.

Reference is made to FIG. 7, which illustrates a number of possible paths through the directed graph; each path representing a possible edited image sequences, according to an embodiment of the invention. FIG. 7 illustrates a number of valid paths 720, 730, and 740 through the directed graph 610 each of the paths may be associated with possible edited image sequences according to an embodiment of the invention.

Illustration 720 may represent an initial image sequence, for example, prior to removing frames determined to be captured during oscillating motion of the imaging device. Illustration 720 may represent a possible path that visits each node of the graph. The associated edited image stream is the stream that includes all original frames. i.e., no valid jump candidates are chosen to be excluded from the image stream. For example, all frames represented by path 720 through the directed graph (e.g., frames 721 to 723) may be selected (e.g., none of the jump candidates marked as $l_n$ are selected).

Each possible path through the graph may be associated with a possible image stream editing; frames associated with visited nodes may be kept as part of the stream, while frames associated with non-visited nodes may be removed from the image stream.

Illustration 730 shows a path associated with a valid sub-set $\{l_i, l_2, l_3, l_4\}$ of a number of valid jump candidates. All or a portion of the jump candidates may be selected to be excluded from the initial image sequence. The remaining image frames in the edited image sequence (e.g., images not selected for exclusion) may have been captured during substantially unidirectional forward motion of the imaging device. When jump candidate(s) are excluded, the non-consecutive preceding and succeeding frames from the initial image sequence may be merged or become consecutive in the edited image sequence. In another embodiment, instead of or in combination with deletion or merging of frames, frames may also be re-ordered according to their relative position along the GI tract or distance from the reference point in the GI tract.

An edited image sequence may include gaps, skips or jumps in the time or frame number (x-axis) associated with the deleted image segments. For example, an edited image stream associated with path 730 may include a jump from frame 733 to frame 734 in the initial sequence, which may create a gap of frames which were captured therebetween. Non-consecutively captured frames 732 and 735 may be consecutively ordered in the edited image sequence. Jumps may skip from one frame to another non-consecutive frame that images the same position or an advanced position along the GI tract (e.g., having the same or similar y-axis value(s)) and/or moving in the same direction (e.g., having a point in the graph 600 with the same sign (+) or (−) of the derivative function at that point).

Illustration 740 may represent a path that is associated with a valid sub-set $\{l_i, l_2, l_7, l_6, l_5, l_4\}$ of valid jump candidates different than the one selected in illustration 730. The number of frames remaining in the edited image sequence (e.g., not contained in the jump) using the jump candidates in illustration 740 is different (e.g., less) than the number of frames remaining in the edited image sequence using the jump candidates in illustrations 730 and 720.

In one embodiment, the optimal sub-set of valid jump candidates that leave the smallest number of remaining images in the edited sequence may be selected to minimize viewing time of the edited movie or image stream. The selection of the optimal valid sub-sets of valid jump candidates may be done through finding the shortest path on the associated directed graph, using one of the above mentioned algorithms. In such embodiments, since the deleted jump segments image already imaged areas of the GI tract, substantially no important information may be deleted when editing the initial image stream to generate the shorter edited image stream.

After estimation of the relative position per each frame is accomplished, e.g. after graph 600 is built, and before the associated directed graph 610 is built, a set of valid jump candidates or loops may need to be identified. In order to do so, jump candidates or loops may first be identified and then validity of each and every one of them may be verified, separately. A number of filters may be used in order to perform validation verification of the jump candidates, and thus to reduce the number of jump candidates. The filtering process may have a number of purposes:

(I) taking into account accumulative error of progress estimation (and thus verifying no substantial tissue coverage loss), (II) ensuring that if frames of a loop are excluded, the resulting image stream or video appears as a natural flow, and (III) reducing the otherwise potentially un-traceable large amount of jump candidates.

Other or different purposes may be used. In order to reduce the number of jump candidates (and thereby to reduce processing time and complexity), some of the jump candidates may be determined to be invalid jumps. Since the initial jump candidate filter may run computations on all (or most) frames in the initial image sequence (e.g., up to 300,000 frames), relatively simple calculations (e.g., as defined in equation (3)) may be used in initial filters in order to reduce the number of possible jump candidates. Whereas, one or more secondary filters, which may be more computationally intensive, may be run on the reduced number of jump candidates (e.g., 25,000-50,000 frames).

Figure 8:
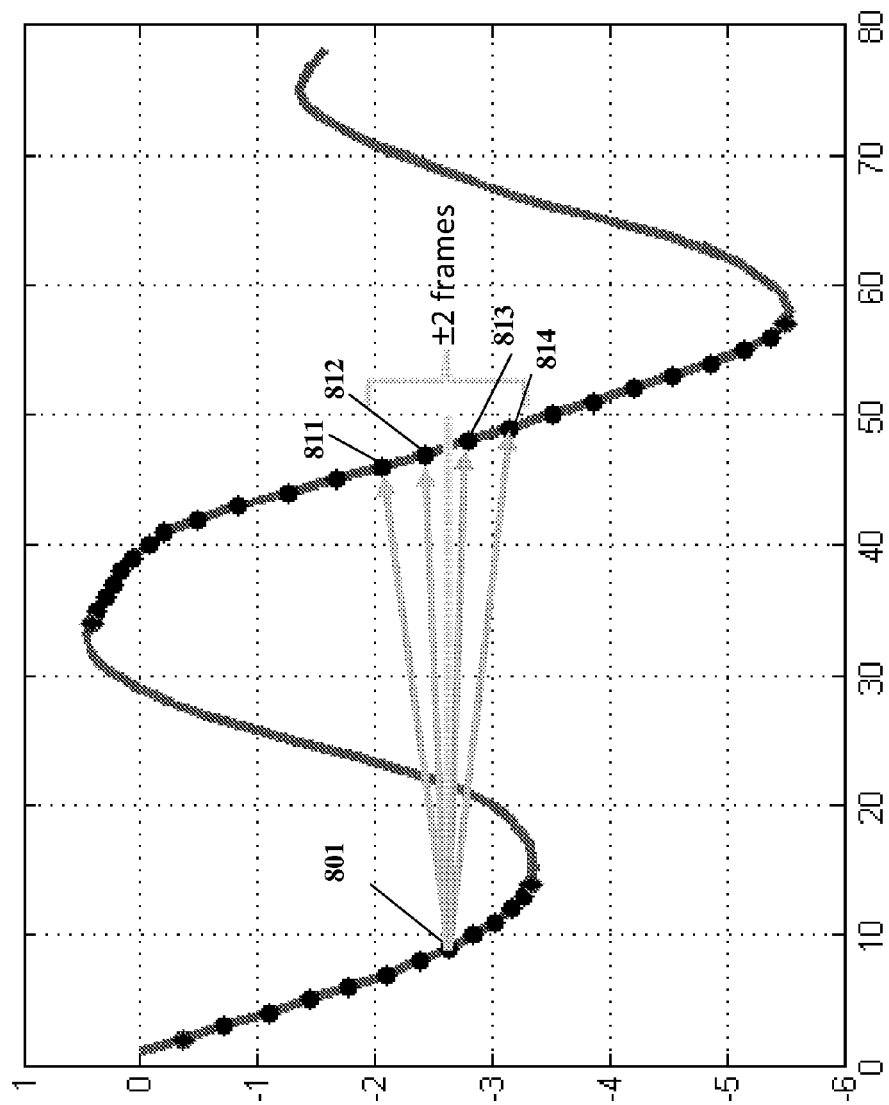
FIG. 8 is a schematic illustration of a selection of initial jump candidates according to an embodiment of the invention.

Reference is now made to FIG. 8, which is a schematic illustration of a selection of initial jump candidates according to an embodiment of the invention. Due to the discrete (non-continuous) nature of the progress estimation graph, it is possible that none of the frames are captured at the exact same position of the in-vivo imaging device along the GI tract. In order to overcome this difficulty and the difficulty as described in purpose (I) above, the following process may be used:

(1) a horizontal line may be drawn for any frame, e.g. frame 801, such that the line begins at frame 801 and reaches the end of the sequence of frames;

(2) for each location where the graph (illustrating the sequence progress estimation) intersects with the horizontal line, two frames (or any other number) preceding the intersect and two frames (or any other number) succeeding the intersect may be identified.

(3) Four jump candidates may be defined, e.g. frame 801 may be the first frame for all four jump candidates, while the last frame of the jump candidates may be selected from: 811, 812, 813, and 814.

In other embodiments, other numbers of preceding and succeeding frames may be selected, with respect to the intersect location. The number of defined jump candidates may change according to the number of identified preceding and succeeding frames.

The larger the number of corresponding preceding/succeeding frames, the higher the chance is that at least one of the defined jump candidates eliminates substantial coverage loss. On the other hand, the larger the number of corresponding preceding/succeeding frames, the higher the chance of defining an untraceable large set of jump candidates. Therefore, the selection of two preceding frames and two succeeding frames may be a reasonable compromise.

Figure 9:
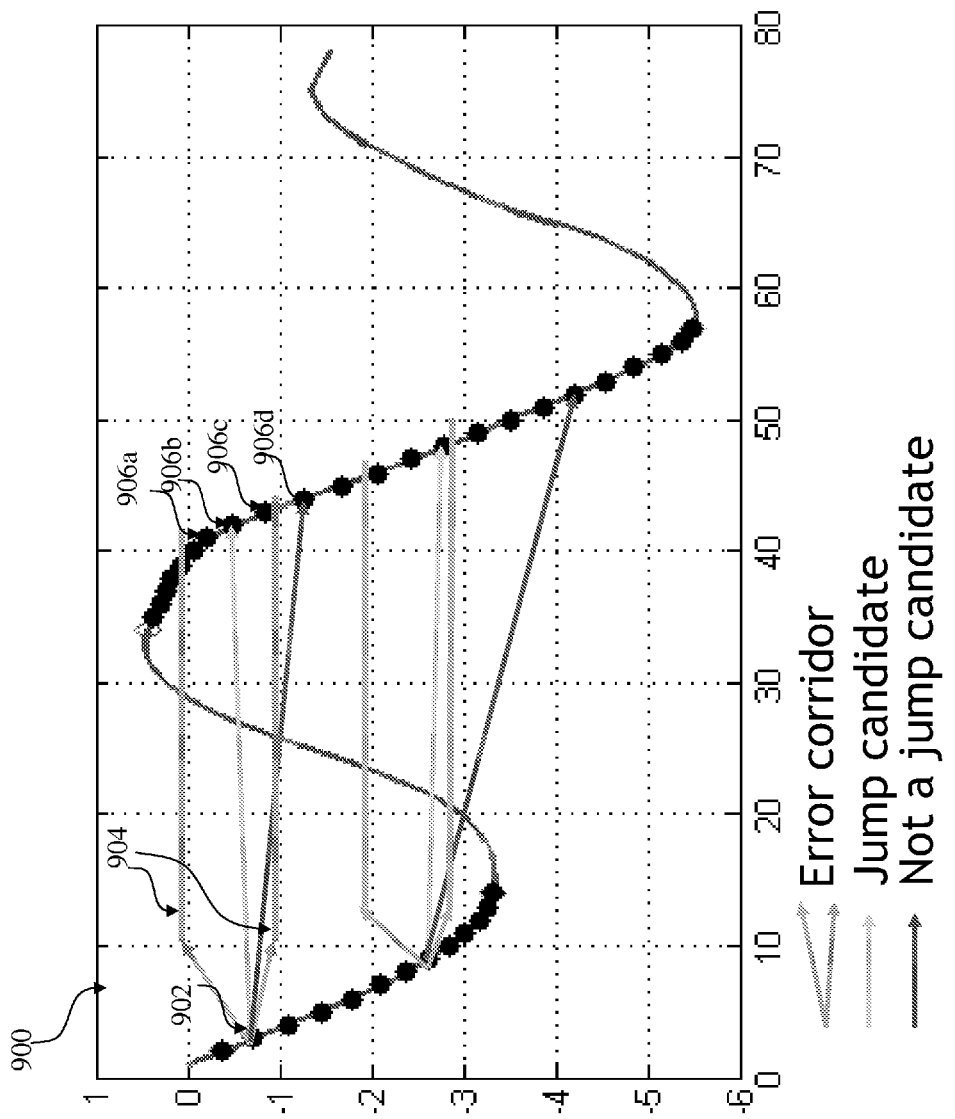
FIG. 9 is a schematic illustration of a selection of initial jump candidates according to another embodiment of the invention.

Reference is made to FIG. 9, which is a schematic illustration of a selection of initial jump candidates according to another embodiment of the invention. Graph 900 may illustrate an alternative process that may be used in order to overcome the discrete nature of the progress estimation graph and possible coverage loss as described in purpose (I) above. Graph 900 may illustrate a process different than the process described in graph 800. In this embodiment, a predetermined maximum difference between y coordinates of the first and the last frame of the jump candidate may be defined. According to graph 900, point 902 corresponds to the first frame of a jump candidate, while any of 906a, 906b, and 906c may correspond to the last frame of the jump candidate. However, 906d may not be considered as the last frame of the jump, since its y coordinate is substantially different from the y coordinate of point 902. That is, the difference between the y coordinates of 902 and of 906d is larger than the predetermined maximum difference. The last frame of the jump candidate, e.g. 906a, 906b, and 906c may be on a segment of a succeeding peak of the graph 900 (e.g., separated by at least one local minimum) where the segment has a (e.g., negative) slope indicating forward motion.

The larger the predetermined maximum difference is, the higher the chance is that at least one of the defined jump candidates eliminates substantial coverage loss.

Figure 10:
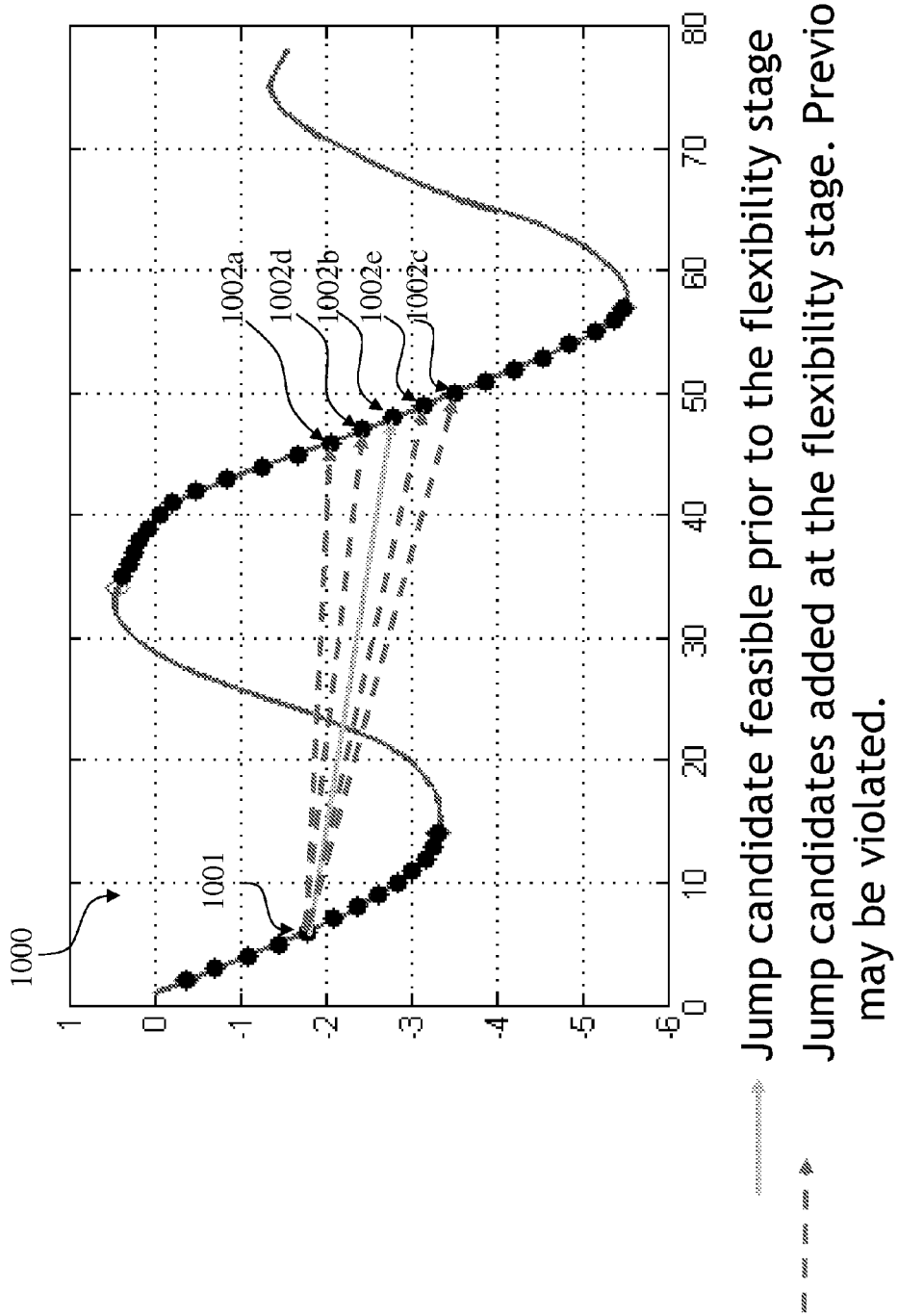
FIG. 10 is a schematic illustration of a flexibility stage where a number of initial jump candidates is enlarged, according to an embodiment of the invention.

Reference is made to FIG. 10, which is a schematic illustration of a flexibility stage, where a number of initial jump candidates is enlarged, according to an embodiment of the invention. FIG. 10 includes progress estimation graph 1000 and demonstrates a flexibility stage in defining additional jump candidates. This stage may be used in order to further address possible coverage loss.

In one embodiment, a flexibility stage (e.g., shown in FIG. 10) may be added to offer additional jump candidates per each initial jump candidate (e.g., as shown in FIG. 8 or in FIG. 9). In some embodiments, the first frame of the additional jump candidate may be identical to the first frame of the initial jump candidate. The last frame of the additional jump candidates may be selected from a predetermined number of frames preceding the initial jump candidates' last frame, as well as an equal number of frames succeeding the initial jump candidate's last frame. For example, for an initial jump candidate, which includes 1001 as its first frame and 1002b as its last frame, embodiments of the invention may provide four new jump candidates, e.g. a first jump candidate between frames 1001 and 1002a, a second jump candidate between frames 1001 and 1002c, a third jump candidate between frame 1001 and 1002d and a forth jump candidate between frame 1001 and 1002e. Any other number of new jump candidates may be provided. In the example above, the predetermined number of frames preceding the initial jump candidate's last frame is two and the predetermined number of frames succeeding the initial jump candidate's last frame is also two.

The flexibility stage may either be ignored, executed once or may be used iteratively during the jump candidates' creation process or during the jump candidates' filtering process.

Following the operation of generating jump candidates, there may be an operation of filtering the jump candidates in order to generate a set of valid jump candidates. In one example, a computationally simple filter may be used in order to reduce the number of jump candidates. Such a filter may verify that a jump candidate includes a start frame and an end frame, both of which were captured while the capsule was traveling in substantially the same (forward) direction. In addition, the filter may verify that the start and end frames are of similar velocity or speed (e.g., the image capture device had the same or similar speed when capturing the start and end frame), in order to ensure smoothness and natural flow of the edited movie or image stream. Similar speeds may be determined, for example, as speeds within a specific range. For example a speed of the start frame may be $V_{start}$, and the speed of the end frame may be $V_{end}$. Determining similar speeds may be performed, for example, by determining a certain range of similar speeds, e.g. the range between $(V_{start}-c)$ to $(V_{start}+c)$, wherein c indicates a constant. Other ranges may be determined, for example the speed of the end frame may be used for determining the range. The speed or velocity of a frame is the speed or velocity of the device having captured the frame (e.g., capsule 40) at the time of the capture of the frame. For example, a valid jump candidate $l_i$ (in graph 600) may include all image frames imaging regions between frames 601 and 602, while an invalid jump candidate may include all image frames imaging regions between frames 601 to 603. Jump candidate between frames 601 to 603 may be invalid because according to graph 600, in frame 601 the in-vivo imaging device is moving forward, whereas in frame 603 the in-vivo imaging device is moving backwards.

Another filter, according to another embodiment, may monitor one or more motion parameters, e.g., the speed and/or direction of the imaging device during capturing the start and end frames of each jump candidate. Any sudden changes or jumps in the image sequence (e.g. change of the "speed" of the image sequence's frames) may be more visible in these areas and may, for example, draw un-necessary attention of the reviewer to these areas. Accordingly, if the derivative of the position estimation function at a point (x,y) in graph 600 is approximately zero, then the jump candidate may be determined to be invalid. For example, frames 604, 605 and/or 606 may be determined to be invalid as start or end points for jump candidate frames. These frames may be determined to be invalid since it may be difficult to determine whether the device imaging those frames is moving in a forward or backward direction. These frames may also be determined to be invalid since the speed of the device imaging those frames is substantially slow in these areas, e.g., the capsule is static or almost static.

Figure 11:
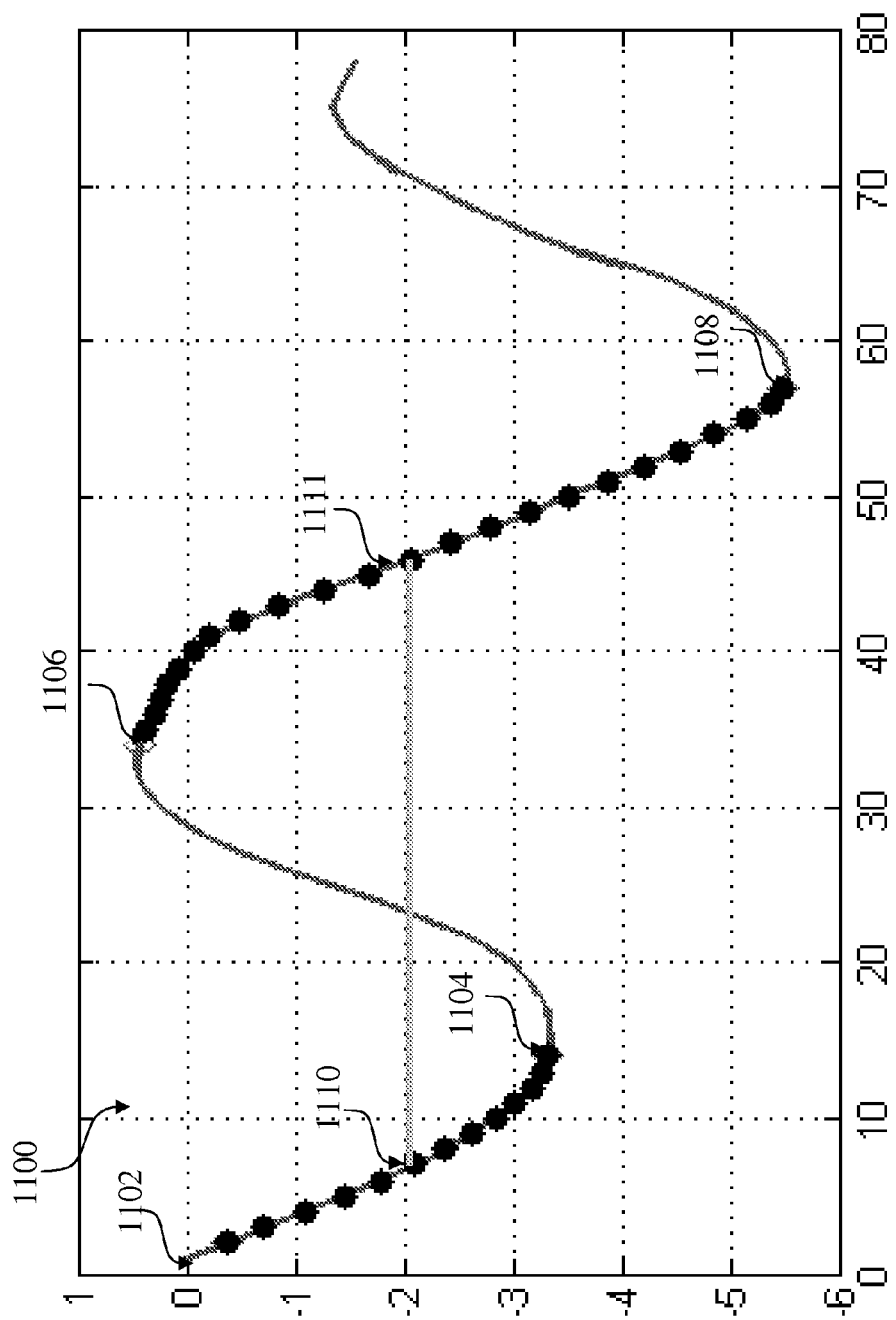
FIG. 11 is a schematic illustration of a jump candidate filter, based on estimated imaging device velocity or speed, according to an embodiment of the invention.

Reference is made to FIG. 11, which is a schematic illustration of a jump candidate filter, based on estimated imaging device "speed", according to an embodiment of the invention. FIG. 11 includes a progress estimation graph 1100. As described above, a jump candidate filter should enable jumps between frames of significant speed (e.g., between frames 1110 and 1111). In order for such a jump candidate selection to be more robust and stable, a filter may enable selection of jump candidates where not only the speed of the first and last frames of the jump is significant, but rather where each of the first and last frames of the jump candidates are included in a sequence of frames with significant speed. For example, first frame 1110 may be a part of continuous sequence of "fast frames", e.g. between frames 1102 and 1104. Likewise, last frame 1111 may be one frame in another continuous sequence of "fast frames", e.g. between frames 1106 and 1108. In some embodiments, a frame i may be considered as a "fast frame" if $|d(i-1, i)|$ is larger than a predetermined threshold, e.g. 0.03.

Figure 12:
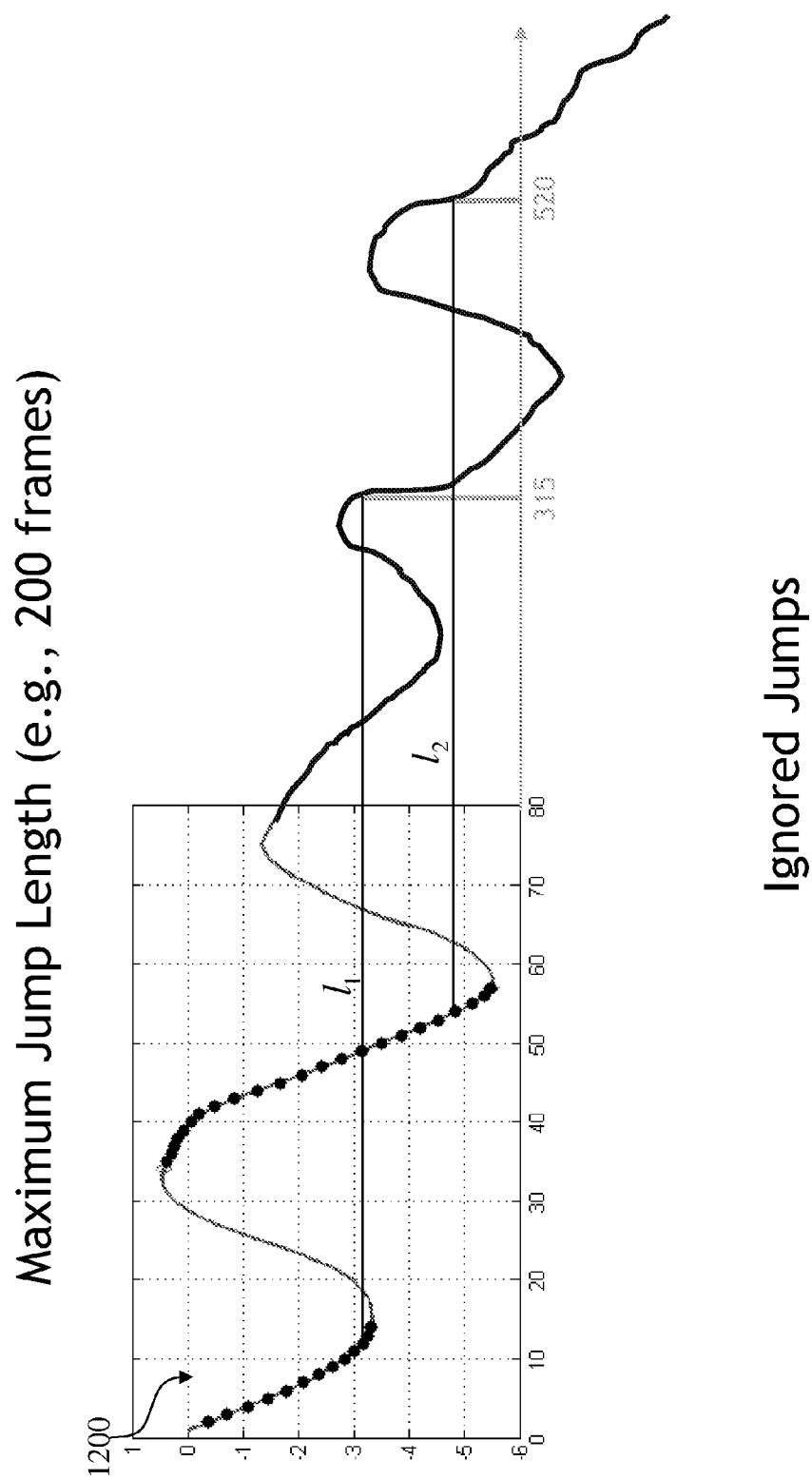
FIG. 12 is a graph that illustrates a maximum jump candidate length when editing an image stream, according to an embodiment of the invention.

Reference is made to FIG. 12 which is a graph that illustrates a maximum jump candidate length when editing an image stream, according to an embodiment of the invention.

In some embodiments, jumps may span a relatively large number of frames, as shown in FIG. 12. In such embodiments, the accumulative error may render the jump candidate invalid. For example, despite the same (y) coordinates of the progress estimation graph 600, the first and the last frame of the jump candidate may have in fact been captured in significantly distant GI tract regions. Deleting such a jump candidate may result in a substantial loss of data and/or may create gaps which may appear jittery to the viewer. Therefore, a jump candidate filter may define the maximum length of a jump candidate, e.g. such a filter may define the maximum number of frames included within a jump candidate. When the number of frames of a jump candidate exceeds the maximum limit, the jump candidate is considered invalid and may not be used to delete frames.

FIG. 12 may include a progress estimation graph 1200. In the example illustrated in FIG. 12, a maximum length of a jump candidate may be defined as 200 frames. Therefore, jump candidates $l_1$ and $l_2$ are invalid, since their length exceeds 200 frames. In alternate embodiments a maximum need not be used.

The number of frames of the maximum jump limit may be set manually, for example, by a user or programmer, or may be dynamically adjusted by a processor, for example, based on statistical data of deleted frames. For example, to generate an edited image stream of a predetermined fixed length, the processor may delete frames at a constant average rate. Thus, if frames have previously been deleted at a lower than average rate (e.g., due to a greater than normal detection of potential pathologies), the maximum number of frames for a jump may be increased to increase the potential number of frames that may be deleted during further editing.

Figure 13:
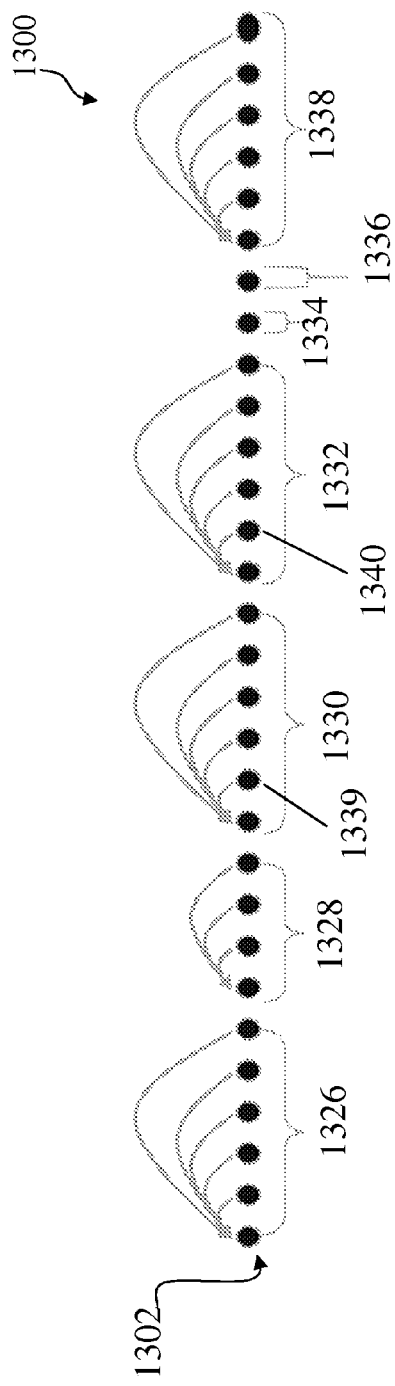
FIG. 13 is a schematic illustration of an image stream sequence divided into a number of short sub-sequences, according to an embodiment of the invention.

Reference is made to FIG. 13, which is a schematic illustration of an image stream sequence 1302 divided into a number of short sub-sequences (e.g., 1326, 1328, 1330, etc.), according to an embodiment of the invention. In one embodiment, the image stream 1302 may undergo the following labeling process in order to be divided into short sub-sequences:
Initialization:
$i_0=1$;
$i=1$;
count value=1;
first frame of the image stream is labeled as 1.
Until i<=(number of frames in the image stream):
i=i+1
registration between $i_0$ and i is attempted;
If fail:
count value=count value+1
$i_0=i$
frame i is labeled as count value
Finalization:
Frames with the same label are grouped into sub-sequences.

An arrow in FIG. 13 illustrates a successful registration attempt. In FIG. 13, sub-sequence 1326 is an example of a group of frames with the same label. Frames with a different labels may not be grouped into a sub-sequence, e.g., frames 1339 and 1340. In some embodiments, a jump candidate filter may limit the number of such sub-sequences that may be included within a valid jump candidate.

Another filter that may be used to reduce the number of valid jump candidates may verify that frames separated by the jump candidates are captured at the same GI area, in order to overcome coverage loss. This may be done by verifying similarity between the first frame of the jump candidate and the last frame of the jump candidate. Similarity criteria may measure any similarity (or dissimilarity) between a current frame, pixel set, portion of the current frame, or image stream segment, and another, preceding, subsequent, reference, averaged, merged, or default, frame, pixel set, portion, or segment. Similarity criteria may measure the differences in pixel color between histograms of images for example using Earth Movers Distance (EMD) method, differences between the current image segment and another image segment, variance in image differences, and/or a similarity rank or score. In one example, similarity criteria may measure the similarity, presence or location of a target object, such as, anatomical features (e.g., polyps), in each frame. In another example, similarity criteria may measure the similarity in the size, circumference or number of pixels associated with the lumen opening (e.g., dark pixels) or the lumen wall (e.g., bright pixels). Other or different measures of the similarity may be used.

Similarity criteria may be measured using all of the pixels in the frames or, alternatively, only a subset of the pixels in the frames, for example, at predetermined coordinate locations known typically to have the most varying values or identified to image anatomical features. In another embodiment, similarity criteria may be computed using data from a header, prefix, suffix, or another summary frame information package associated with the compressed image frames. The compressed frame headers or other compressed portions may include one or more thumbnails, a RGB (red-green-blue) sum value, a RGB difference value, an analog gain value, an exposure value, and other features or metadata. One or more items of compressed data may be used, e.g., compressed RGB difference values. Analyzing compressed frame headers or some data within such headers may be faster (though potentially less accurate) than analyzing uncompressed frame data. In this and other embodiments described herein, information in a "header" may be placed in various forms of summary information packages, such as a prefix or suffix.

A verifying filter based on similarity criteria may include, for example, an attempt to perform registration between the first frame of the jump and the last frame of the jump. Successful registration may identify a jump candidate as valid, while un-successful registration may identify a jump candidate as invalid. Since the registration process may be computationally expensive (e.g. time consuming), this may be used at a later stage, e.g. as one of the filters used towards the end of jump candidate verification procedure.

Another verifying filter based on similarity criteria may be defined using EMD method, that is, EMD may be estimated between the first and last frames of the jump candidates. If the EMD value is above a (predetermined) threshold the jump candidate may be considered an invalid jump candidate.

Figure 14:
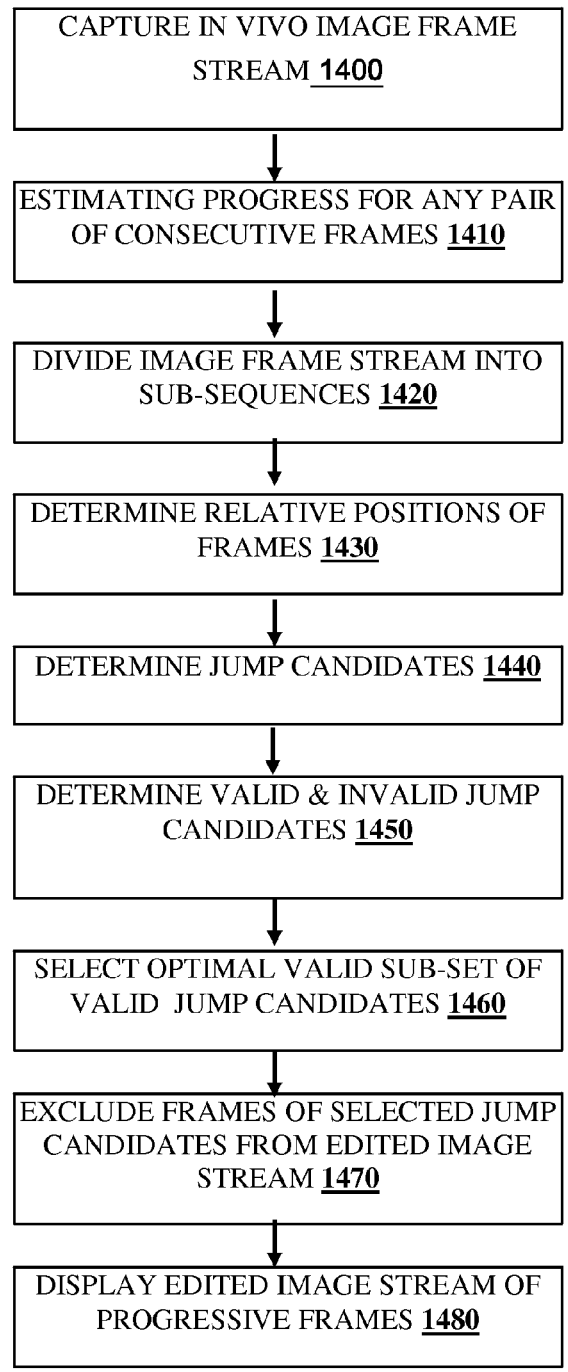
FIG. 14 is a flowchart of a method, according to an embodiment of the invention.

Reference is made to FIG. 14, which is a flowchart of a method for editing an image stream, according to an embodiment of the invention. The image stream may be captured by an in-vivo imaging device and may include a number of image frames.

In operation 1400, an autonomous imaging device (e.g., device 40 of FIG. 1, although devices and systems other than that shown in FIG. 1 may be used) may capture in vivo image frames while passively traversing the gastro-intestinal tract (e.g., from the mouth to the anus in a single passage). The device may capture a sequence of images (or image frame stream) at sequentially increasing respective times (e.g., defined by a total elapsed time from the start of the image sequence or sub-sequence or an absolute time, or other measures). The imaging device may include a transmitter, which may wirelessly transmit the captured images while (or after) traversing the GI tract from inside a patient's body to a receiver disposed outside the patient's body. The captured images may be stored in a storage unit (e.g., storage unit 16 or 19 of FIG. 1) from which the processor may accesses the captured images. The frames may be combined consecutively to form a moving image stream.

In operation 1410, a processor (e.g., data processor 14 or 15 of FIG. 1) may run a pre-process of estimating progress of the imaging device along the longitudinal axis of the GI tract between any pair of consecutive frames (e.g., as defined by equation (3) and based on the registration process). For some pairs of consecutive frames, the progress estimation may fail (e.g., the registration failed).

In operation 1420, a processor (e.g., data processor 14 or 15 of FIG. 1) may define sub-sequences of the captured image stream such that for each pair of consecutive frames of the sub-sequence, the progress estimation was established successfully. That is, this operation divides the entire captured image stream into sub-sequences of frames. In some embodiments, each of the following operations may be performed for each sub-sequence separately, without being dependent on the results of the other sub-sequences.

In operation 1430, a processor (e.g., data processor 14 or 15 of FIG. 1) may determine the relative positions or distances of the imaging device during the frame capture, for example, from a reference point (e.g., a position of the imaging device during capture of a reference image along the GI tract). The distance between the positions of the imaging device during capture of two frames, may be estimated using the results of 1410 (e.g., as defined by equation (4)). The relative positions of frames may be presented, for example, by progress estimation graph 600 of FIG. 6.

In operation 1440, loop or jump candidates may be determined as sequences of consecutive frames, where the first frame of the sequence and the last frame of the sequence may have the same (y) coordinate, on the progress estimation graph 600, built according to step 1430. In some embodiments, jump candidates may include oscillating motion segments. In addition, the GI tract regions covered by the frames of the jump candidate, are also covered in other sequences or portions of the captured image stream.

In some embodiments, a flexibility stage may provide additional jump candidates. The flexibility stage may be used to refine the jump selection, for example, by providing extra jump candidates per each existing jump candidate. For example, during flexibility stage the first frame of an existing jump candidate may be the first frame of the additional jump candidates, while the last frame of each additional jump candidate may be selected from frames preceding (e.g., coming before in time) and succeeding (e.g., coming after in time) the last frame of the existing jump candidate.

In operation 1450, a series of filters or parameters may be used in order to determine validity or invalidity of each jump candidate, separately. In some embodiments, several parameters or filters may be used in combination. For example, a filter based on registration may verify that the non-consecutive frames preceding and succeeding the potential jump actually match so that deleting the frames would generate a smooth transition for the viewer of the edited image stream. A filter may compare the preceding and succeeding frames based on one or more predetermined similarity criteria, other than registration, for example, EMD. In one embodiment, a filter based on similarity criteria may compare the frames preceding and succeeding each jump candidate and mark the jump candidate as valid or invalid, based on the result of the comparison.

In some embodiments, jump candidates may be valid that include start and end frames captured while the imaging device moves in the same direction and/or with the same or similar speeds along the GI tract main axis. In some embodiments, jump candidates may be valid if the derivative of the progress estimation graph (e.g., graph 600 of FIG. 6) at the start and end frames are negative. In some embodiments, jump candidates may be valid if the remaining frames (e.g., remaining in the edited image stream) maintain a substantially smooth flow of the image stream, e.g., without sudden or abrupt changes in speed or scenery.

Operation 1440 and operation 1450 may comprise a series of steps. In some embodiments, some of the steps of operation 1440 may be performed after some of the steps of operation 1450.

In operation 1460, an optimal valid sub-set of valid jump candidates may be selected, for example, to remove repetitive image sequences from the image stream and generate the edited image stream. The optimal valid subset of valid jump candidates may be selected such that the generated edited image stream has the minimal amount of remaining frames (e.g., such that the largest possible amount of frames are removed from the image stream).

The optimal valid sub-set of valid jump candidates selected to edit from the image sequence may be selected by an editing mechanism, for example, solving the "shortest path" problem of graph theory on an associated directed graph (e.g. graph 610 of FIG. 6). To define the directed graph (e.g. graph 610), solve the "shortest path" problem, and select an optimal valid sub-set of valid jump candidates, the processor may execute, for example (other operations may be used):

Define a node $n_i$ for each frame F.
Define a directed edge $n_i \rightarrow n_{i+1}$ for each pair of consequent frames $F_i$, $F_{i+1}$.
Define a directed edge $n_i \rightarrow n_j$ for each valid jump candidate (loop) between frames $F_i$ and $F_j$.
Define a "source" and "sink" to be the nodes that correspond to the first frame of the sub-sequence and the last frame of the sub-sequence, respectively (sub-sequences as defined in operation 1420).
Solve the "shortest path" problem specified by the "source" and "sink" as defined in the previous step.
Select valid jump candidates associated with the "shortest path" found in the previous step.

In operation 1470, the jump candidates (e.g., oscillations) selected in operation 1460 may be excluded or deleted from an initial image stream, thus the initial image stream is edited. Excluding the jump candidates may include excluding the repetitive frames included therein, from the image stream, or excluding frames of regions in the GI which have been imaged a plurality of times by the imaging device during a single imaging procedure. In some embodiments, excluded image sequences may correspond to detected oscillating motion segments. For example, the excluded image sequences may be selected from the detected oscillating motion segments, e.g. since each jump candidate is associated with (e.g. selected from) frame sequences which correspond to an oscillating motion segment. In some embodiments, the repetitive frame may be excluded that has worse frame clarity. The non-consecutively captured frames preceding and succeeding the excluded jump candidate may be merged or viewed consecutively to show motion through the GI tract. In some embodiments, the selected jump candidates may be removed from the collection of displayed images, which may not necessarily be displayed as a moving image stream or movie. For example, the edited image stream may be displayed as a sequence of still images on the display.

In operation 1480, a monitor (e.g., monitor 18 of FIG. 1) may display the edited image stream. The edited image stream may include exclusively or mostly progressive frame segments or frames captured by a device traveling with forward motion. The monitor may display each frame at an equal viewing rate. Alternatively, the monitor may display each frame for a duration of time which is proportional to the distance traveled between that frame and the preceding frame. In this way, the distance imaged along the GI tract may be viewed constantly over time.

Other operations or orders of operations may be used.

When used herein, operations, detectors and other processes may be processes executed by a processor (e.g., processor 14 or 15 of FIG. 1) or may be other processes, e.g., carried out by dedicated hardware.

Embodiments of the invention may include identifying duplicate passes having repetitive frames, where the first and second pass sequences image the same or overlapping regions of the GI tract. For example, each pass may include at least one frame imaging at a position already imaged in the other pass sequence. Once the duplicate passes are identified the processor or process may proceed in any manner, for example, deleting one of the passes (e.g., the later pass or the pass with worse image quality), rearranging the frames of the duplicate passes so that repetitive frames from the respective passes are sequenced consecutively, or merging a number of repetitive frames from the respective passes into a single frame. Other ways of determining motion or position may be used (e.g., radio triangulation of received transmissions from the imaging device, etc.) and other ways of tracking objects may be used.

Embodiments of the invention may work in conjunction with or may be overridden by other modules or editing tools. For example, certain modules may select images, e.g., depicting potential pathologies, that may not be deleted regardless of the (forward or backward) direction of motion of the device capturing the frame.

Embodiments of the invention may monitor other measures of motion, such as speed, acceleration, rotation, orientation, etc. These motion factors may be used to determine oscillating motion instead of or in addition to position. For example, additional motion factors may be used as a double check of other oscillating motion detectors. For example, a change in direction should coincide with zero speed.

In one embodiment, the processor may use a scoring system to match and quantify frame similarity features. When used herein, a "score" or "match" value may be a general rating, where (in one embodiment) the closer the "scores" between frames the greater the overall similarity therebetween, and (in another embodiment) a score may be associated with a specific property, e.g., a color score, a pathology score, a contraction type, rate or frequency score, or another score or measure that indicates a specific feature in the sequences. The individual scores of the frames or sequences may be combined as a relative score measuring the similarity between the frames or sequences. Similarity scores may represent, for example, a (normal or weighted) average of the difference in features between the captured and template sequences.

A score, rating, or matching value may be a simplified representation (e.g., a derived value or rating, such as an integer 1-100) of more complex characteristics of an image or a portion of an image (e.g., criteria, such as, color variation, appearance of certain textural or structural patterns, light intensity of the image or portions thereof, blood detection, etc.). A score may include any rating, rank, hierarchy, scale or relative values of features or criteria. Typically a matching value is a numerical value, for example, a number from 1 to 10, but need not be limited as such. For example, matching value may be any score in any scale including, for example, a letter (A, B, C, . . . ), signs or symbols (+, −) or computer bit values (0, 1) for forward and backwards motion, for example, indicated by the status of one or more computing flags. Scores may be discrete (non-continuous) values, for example, integers, a, b, c, etc., or may be continuous, for example, having any real value between 0 and 1 (subject to the precision of computer representation of numbers). Any interval between consecutive scores may be set (e.g., 0.1, 0.2, . . . , or 1, 2, . . . , etc.) and scores may or may not be normalized.

Embodiments of the invention describe detecting position or distance traveled between frames based on estimating a distortion between consecutive frames captured by a single imager (e.g., as defined by equation (3) and based on the registration process). However, any other position or distance estimator may be used. For example, in some embodiments, the optical properties (e.g., focal length) of an imager may be used, in a combination of other factors, to determine the imager's distance to the lumen wall (or this distance may be approximated), per each frame. The difference of these distances for any two consecutive frames may be used to determine the distance between these frames. In another example, the distance or direction of device movement between frames may be detected using (e.g., two) opposite facing imagers. Opposite facing imagers typically capture similar images (or features thereof) at a time lag. The time lag may be predetermined and/or fixed based on the spacing between the imagers and/or the frame capture rate. In one embodiment, the imager that captures similar images or features at an earlier time may be a "forward" facing imager (more advanced along the GI tract), while the other imager may be a "rear" facing imager. Once the forward and rear orientation of the imagers is determined, when a processor detects that the forward facing imager captures the similar images or features at a later time than the rear facing imager (e.g., approximately equal to the predetermined time lag), the processor may determine that the imaging device is traveling in a reverse direction. Accordingly, the processor may track similarity features of frames captured by the opposite facing imagers, e.g., in parallel, to detect non-progressive motion.

In another embodiment, a number of electrodes or other motion-dedicated detectors separated by a distance along the length of the device body may be used to detect the direction of motion based on cross-correlated electrode or other signal patterns.

In some embodiments, the imaging device may be configured to prevent capture of oscillating motion frames in real time by deactivating the imager, decreasing the frame capture rate, or powering down transmission, illumination or other device units when oscillating motion is detected. The deactivation or decreased power modes may be sustained for a predetermined "back-out" period of time (e.g., measured by an internal clock) or may be abandoned when progressive motion is detected again, for example, to reactivate the imaging units or increase the frame capture rate.

In another embodiment, instead of deleting oscillating frame sequences, the editing module may reorder or rearrange (some or all) oscillating frame sequences into a new progressive order. Frames may be reordered so that sequential frames in the new order image sequentially progressive positions of the GI tract. Thus, image segments associated with jump candidates may instead be replaced by frames captured out of order in time or frame number, but which image regions in order of increasing (progressive) positions along the GI tract. Other actions may be taken.

Deleting or re-ordering frames may generate skips or jumps in the visual content of newly joined frames. Embodiments of the invention may smooth skips. For example, a "dummy frame" may be introduced between the start and end frames of a jump candidate. Affine transformation matrix between the start and end frames of the jump candidate may be a combination of a first affine transformation matrix between the start frame and the "dummy frame", and a second affine transformation matrix between the "dummy frame" and the end frame of the jump candidate. The first and second affine matrices should be as similar as possible in order to achieve a smoother image stream appearance.

Position may be one-dimensional (1D) and may measure a 1D motion, for example, along the transverse or central longitudinal axis of the GI tract. Representing 3D motion by a 1D simplification may be sufficiently accurate for detecting oscillating motion while simple enough to reduce memory load and data computation. In other embodiments, 2D or 3D position and motion functions may be used.

Embodiments of the invention may include an article such as a non-transitory computer or processor readable medium, or a non-transitory computer or processor storage medium, such as for example a memory, a disk drive, or a USB flash memory, for encoding, including or storing instructions which when executed by a processor or controller (for example, data processor 14 of FIG. 1), carry out methods disclosed herein.

Although the particular embodiments shown and described above will prove to be useful for the many distribution systems to which the present invention pertains, further modifications of the present invention will occur to persons skilled in the art. All such modifications are deemed to be within the scope and spirit of the present invention as defined by the appended claims.

The invention claimed is:

1. A method for editing an image stream comprising a plurality of image frames and captured by an in-vivo imaging device that passes through the gastrointestinal (GI) tract, the method comprising:
estimating progress of the imaging device along the GI tract;
based on the estimated progress, detecting oscillating motion segments of the imaging device along the GI tract, wherein oscillating motion includes backward motion segments of the imaging device traveling along the GI tract;
excluding image sequences from the image stream, to produce an edited image stream, wherein the excluded image sequences are selected from the detected oscillating motion segments; and
displaying the edited image stream.

2. The method of claim 1, wherein the detected oscillating motion segments include images of regions of the GI tract, wherein said image regions have been imaged a plurality of times by the imaging device.

3. The method of claim 1, comprising producing a progress estimation graph indicating the estimated progress of the imaging device.

4. The method of claim 3, comprising generating a plurality of jump candidates from the graph, each jump candidate comprising a plurality of images, each jump candidate being associated with a detected oscillating motion segment of the imaging device along the GI tract.

5. The method of claim 4, comprising determining validity of said jump candidates and selecting valid jump candidates.

6. The method of claim 5, comprising selecting a subset of valid jump candidates.

7. The method of claim 5, wherein determining validity of the jump candidates comprises:
comparing a first frame of the jump candidate to a last frame of the jump candidate based on one or more predetermined similarity criteria;
determining that the speed of the imaging device during capture of the first frame of the jump candidate is similar to the speed of the imaging device during capture of the last frame of the jump candidate; and
determining that the first frame of the jump candidate and the last frame of the jump candidate were captured while the capsule was traveling in a substantially forward direction.

8. The method of claim 1, wherein estimating progress of the imaging device comprises estimating a distortion between any two consecutive image frames.

9. The method of claim 1, wherein estimating progress of the imaging device comprises estimating the speed and direction of motion of the imaging device along the GI tract.

10. The method of claim 1, comprising excluding image sequences that have worse frame clarity compared to other image sequences.

11. The method of claim 1, wherein the edited image stream includes image frames captured when the in-vivo imaging device travels with progressive motion.

12. The method of claim 1, wherein the excluded image sequences include images of regions in the GI which have been imaged a plurality of times.

13. A system for editing an image stream comprising a plurality of image frames and captured by an in-vivo imaging device that passes through the gastrointestinal (GI) tract, the system comprising:
a processor to:
estimate progress of the imaging device along the GI tract;
based on the estimated progress, detect oscillating motion segments of the imaging device along the GI tract, wherein oscillating motion includes backward motion segments of the imaging device traveling along the GI tract; and
exclude image sequences from the image stream, thereby producing an edited image stream, wherein the excluded image sequences are selected from the detected oscillating motion segments; and
a monitor to display the edited image stream.

14. The system of claim 13, wherein oscillating motion segments of the imaging device include backward motion segments motion segments.

15. The system of claim 13, wherein the detected oscillating motion segments include images of regions of the GI tract which have been imaged a plurality of times by the imaging device.

16. The system of claim 13, wherein the processor produces a progress estimation graph indicating the estimated progress of the imaging device.

17. The system of claim 16, wherein the processor generates a plurality of jump candidates from the progress estimation graph, each jump candidate comprising a plurality of images, each jump candidate associated with a detected oscillating motion segment of the imaging device along the GI tract.

18. The system of claim 17, wherein the processor determines validity of said jump candidates.

19. The system of claim 18, wherein the processor excludes some of the plurality of image sequences by selecting a subset of valid jump candidates from the plurality of jump candidates, and excluding the frames of the selected valid jump candidates from the edited image stream.

20. The system of claim 13, wherein the processor estimates progress of the imaging device by estimating the distortion between any two consecutive image frames.

21. The system of claim 13, wherein the edited image stream includes image frames captured when the in-vivo imaging device travels with progressive motion.

22. A computer-implemented method for processing an image stream, the method comprising:
- receiving a moving image stream captured by an in-vivo imaging device, the image stream comprising images captured in a GI tract;
- determining the direction of motion of the device;
- based on the images, detecting sequences within the image stream where the device was traveling in reverse motion along the GI tract;
- creating an edited image stream comprising images not within the detected sequences.

23. The method of claim 22, comprising estimating progress of the imaging device, by estimating the distortion between two consecutive image frames.

24. The method of claim 22 wherein the detected image sequences include images of regions of the GI tract which have been imaged a plurality of times by the imaging device.

* * * * *